United States Patent
Shin et al.

(10) Patent No.: US 12,208,098 B2
(45) Date of Patent: Jan. 28, 2025

(54) 4-CARBONYLAMINO-4-PHENYL-PYRIMIDINE COMPOUND OR PHARMACEUTICALLY ACCEPTABLE SALT THEREOF

(71) Applicants: Gachon University Of Industry-Academic Cooperation Foundation, Gyeonggi-do (KR); Gil Medical Center, Incheon (KR)

(72) Inventors: Dongyun Shin, Seoul (KR); Cheol Soo Choi, Incheon (KR); Hee-Sook Jun, Incheon (KR); Cheol Soon Lee, Incheon (KR); Seung-Yong Seo, Incheon (KR); Hojung Choi, Incheon (KR); Sung Jean Park, Incheon (KR); Onnuri Bae, Incheon (KR); Hyunhee Oh, Incheon (KR); Shi-Young Park, Incheon (KR)

(73) Assignees: Gachon University Of Industry-Academic Cooperation Foundation, Gyeonggi-do (KR); Gil Medical Center, Incheon (KR)

( * ) Notice: Subject to any disclaimer, the term of this patent is extended or adjusted under 35 U.S.C. 154(b) by 807 days.

(21) Appl. No.: 17/297,198

(22) PCT Filed: Nov. 26, 2018

(86) PCT No.: PCT/KR2018/014574
§ 371 (c)(1),
(2) Date: May 26, 2021

(87) PCT Pub. No.: WO2020/111283
PCT Pub. Date: Jun. 4, 2020

(65) Prior Publication Data
US 2022/0000868 A1 Jan. 6, 2022

(51) Int. Cl.
*A61K 31/505* (2006.01)
(52) U.S. Cl.
CPC .................. *A61K 31/505* (2013.01)
(58) Field of Classification Search
CPC ....... A61K 31/505; A61K 31/506; A61P 1/16; A61P 3/04; A61P 3/10; C07D 239/42
See application file for complete search history.

(56) References Cited

U.S. PATENT DOCUMENTS

2004/0106634 A1* 6/2004 Satoh ................ A61P 17/02
514/275

FOREIGN PATENT DOCUMENTS

| KR | 20050042478 A | 5/2005 | |
| KR | 20080040027 A | 5/2008 | |
| KR | 20080110998 A | 12/2008 | |
| KR | 101182826 B1 | 9/2012 | |
| WO | 0246170 A2 | 6/2002 | |
| WO | WO-2004041789 A1 * | 5/2004 | ........... C07D 239/42 |
| WO | WO-2007089768 A2 * | 8/2007 | ........... C07D 239/42 |

OTHER PUBLICATIONS

Han, Seung Jin, et al., "b-Cell-protective effect of 2-aminobicyclo-(2,2,1)-heptane-2-carboxylic acid as a glutamate dehydrogenase activator in db/db mice", Journal of Endocrinology (2012) 212, 307-315.

Han, Seung Jin, et al., "Glutamate dehydrogenase activator BCH stimulating reductive amination prevents high fat/high fructose diet-induced steatohepatitis and hyperglycemia in C57BL/6J mice", SciRep. Nov. 22, 2016;5:37468.

Prentki , et al., "Metabolic Signaling in Fuel-Induced Insulin Secretion, Cell Metabolism (2013), http://dx.doi.org/10.1016/j.cmet.2013.05.018".

Stark, Romana , et al., "AMPK and the neuroendocrine regulation of appetite and energy expenditure", Molecular and Cellular Endocrinology 366 (2013) 215-223.

* cited by examiner

*Primary Examiner* — Matthew P Coughlin
*Assistant Examiner* — Meghan C Heasley
(74) *Attorney, Agent, or Firm* — Servilla Whitney LLC

(57) ABSTRACT

The present invention relates to a novel 4-carbonylamino-4-phenylpyrimidine compound or a pharmaceutically acceptable salt thereof. Specifically, the present invention relates to a novel 4-carbonylamino-4-phenylpyrimidine compound or a pharmaceutically acceptable salt thereof, which exhibits GDH activity and as such, is effective for prevention or treatment of obesity, diabetes, or fatty liver.

6 Claims, 1 Drawing Sheet

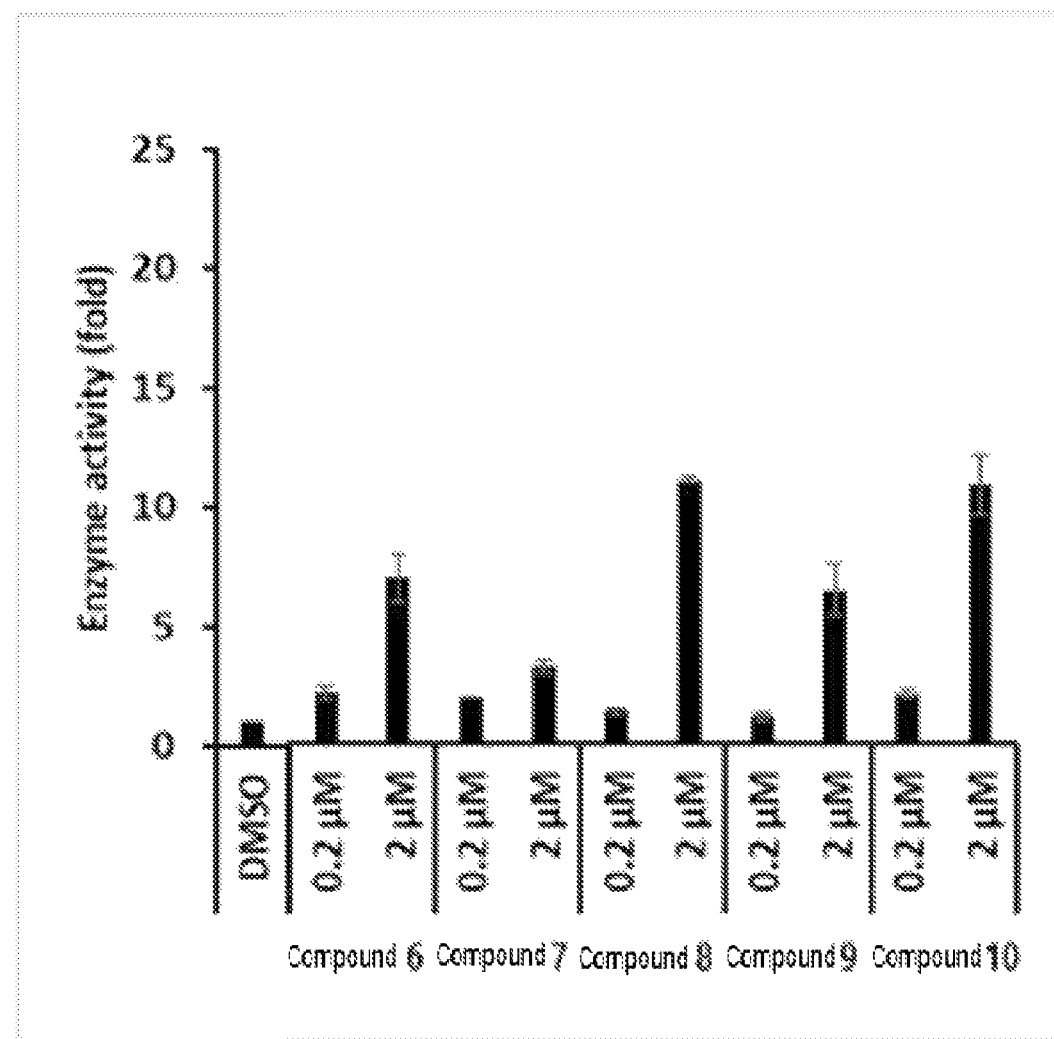

4-CARBONYLAMINO-4-PHENYLPYRIMIDINE COMPOUND OR PHARMACEUTICALLY ACCEPTABLE SALT THEREOF

CROSS-REFERENCE TO RELATED APPLICATIONS

This application is the National Stage entry of PCT/KR2018/014574, filed on Nov. 26, 2018, the entire disclosure of which is hereby incorporated by reference herein.

TECHNICAL FIELD

The present invention relates to a novel 4-carbonylamino-4-phenylpyrimidine compound or a pharmaceutically acceptable salt thereof. In addition, the novel compound of the present invention has an effect of preventing or treating obesity, diabetes, or fatty liver.

BACKGROUND ART

Due to the recent improvement in income level and the development of industry, as lifestyles such as dietary life and eating habits are rapidly westernized, patients with chronic diseases and adult diseases are rapidly increasing, and obesity is known to be one of the causes.

Obesity is an abnormality in energy metabolism caused by an imbalance between energy intake and energy consumption, and as a result, it is defined as an excessive accumulation of triglycerides in fat cells.

Obesity is a chronic disease that is a worldwide problem, and there is no effective treatment method, and it is a serious disease that continues to increase. Obesity, unlike other diseases, is characterized by not only an appearance problem, but also being accompanied by associated diseases such as metabolic disease, hypertension, diabetes, hyperlipidemia, arteriosclerosis, ischemic heart disease, fatty liver, and cholelithiasis as well as weight gain.

Diabetes has become one of the leading causes of adult death worldwide, and the number of patients with diabetes is also rapidly increasing with the increase of the obese population, which is characterized by hyperglycemia due to excessive glucose production and peripheral insulin resistance.

Fatty liver is caused by the accumulation of excessive fat, especially triglycerides, in the liver tissue, and it is generally diagnosed as fatty liver when fat is accumulated by 5% or more of the weight of the liver. Fatty liver is classified into alcoholic and non-alcoholic fatty liver, and non-alcoholic fatty liver is mainly associated with obesity, diabetes, and hyperlipidemia.

A higher arterial stiffness value is shown in 42% of those with non-alcoholic fatty liver than those without non-alcoholic fatty liver. As the degree of fatty liver is serious, a higher risk of arterial stiffness is shown. Thus, it is known that the presence or absence of fatty liver can be also considered as a risk factor for cardiovascular disease.

Glutamate dehydrogenase (GDH) is widely distributed in bacteria, yeast, plants and animal tissues and is the only amino acid dehydrogenase that requires a pyridine nucleotide as a coenzyme. Bacteria and yeast enzymes require NADP+, plant enzymes require NAD+, and animal enzymes such as liver and kidney enzymes require NADP+ or NAD+, and the enzymes do not act on D-glutamic acid or other L-amino acids. There is a pathway for synthesizing L-glutamic acid from D-ketoglutaric acid and ammonia supplied from the TCA cycle, and then synthesizing many amino acids by transfer of the amino group. As such, GDH is an enzyme in an important position connecting the TCA cycle and the amino acid synthesis system.

GDH activators increase the NAD+/NADH ratio in the liver like under fasting or dietary restriction conditions, and as a result of this, increase the activity of AMP-activated protein kinase (AMPK) and sirtuins, and thus, inhibit fatty acid biosynthesis in the liver and gluconeogenesis when fasting. When GDH activator is administered for a long time in a high fat/high fructose diet environment, phosphorylation of JNK, PERK, p38, NFκB, and the like, which induce liver inflammation in the liver, and activation of cytokines are inhibited, and fat accumulation is inhibited, and fatty liver caused by the diet can be prevented (Glutamate dehydrogenase activator BCH stimulating reductive amination prevents high fat/high fructose diet-induced steatohepatitis and hyperglycemia in C57BL/6:1 mice. Sci Rep. 2016 Nov. 22; 5:37468).

In addition, the increase in activity of AMPK and sirtuins is known to improve obesity by regulating energy expenditure and appetite (AMPK and the neuroendocrine regulation of appetite and energy expenditure. Mol Cell Endocrinol. 2013 Feb. 25; 366 (2):215-23).

In pancreatic β-cell mitochondria, GDH increases ArP and citrate in oxidative deamination, thereby increasing depolarization due to the obstruction of ATP-dependent potassium channels and the influx of calcium into cells by voltage-dependent calcium channels, thereby stimulating the secretion of insulin (Triggering pathway), and on the other hand, the increased citrate is converted to acyl-COAs to move insulin prepared in the form of a granule in the cell to the cell membrane to continuously secrete insulin (Amplifying pathway) (Metabolic signaling in fuel-induced insulin secretion. Cell Metab 2013; 18:162-185).

In addition, it is known that, when BCH (2-amino-2-norbornanecarboxylic acid), which increases the activity of GDH, was administered intraperitoneally for a long time in db/db mouse animal model, which is a genetic diabetes model, it not only increased insulin secretion in the pancreas, but also inhibited pancreatic β-cell apoptosis, thereby improving diabetes (β-Cell-protective effect of 2-aminobicyclo-(2,2,1)-heptane-2-carboxylic acid as a glutamate dehydrogenase activator in db/db mice. J Endocrinol. 2012 March; 212(3):307-15 and Korean Patent Registration No. 10-1182826).

Accordingly, the inventors of the present invention confirmed that a novel 4-carbonylamino-4-phenylpyrimidine compound or a pharmaceutically acceptable salt thereof exhibits GDH activity and thus can be used as a therapeutic agent for obesity, diabetes, and fatty liver, thereby completing the present invention.

DETAILED DESCRIPTION OF THE INVENTION

Technical Problem

An object of the present invention is to provide a novel 4-carbonylamino-4-phenylpyrimidine compound or a pharmaceutically acceptable salt thereof that exhibits GDH activity.

Another object of the present invention is to provide a pharmaceutical composition for preventing or treating obesity, diabetes, or fatty liver, comprising a novel 4-carbonylamino-4-phenylpyrimidine compound or a pharmaceutically acceptable salt thereof.

Another object of the present invention is to provide a method for treating obesity, diabetes, or fatty liver, by administering a novel 4-carbonylamino-4-phenylpyrimidine compound or a pharmaceutically acceptable salt thereof to a patient with obesity, diabetes, or fatty liver.

Solution to Problem

The present invention provides a novel compound of formula I below or a pharmaceutically acceptable salt thereof.

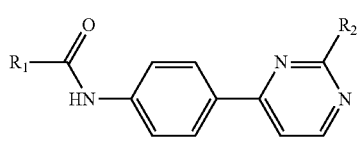

[Formula I]

in which,
$R_1$ is alkyl, alkenyl, alkynyl, cycloalkyl, heterocyclic, aryl, or heteroaryl,
$R_2$ is $NR_3R_4$,
$R_3$ and $R_4$ are independently hydrogen, alkyl, alkenyl, alkynyl, cycloalkyl, heterocyclic, aryl, heteroaryl, alkylcarbonyl, carboxyl, or alkoxycarbonyl,
the cycloalkyl, heterocyclic, aryl, or heteroaryl can be substituted with one or more substituents selected from the group consisting of alkyl, alkenyl, alkynyl, hydroxy, halogen, amino, nitro, cyano, carbonyl, carboxyl, alkoxy, aryl, and aryloxy, and
the alkyl, alkenyl or alkynyl can be substituted with one or more substituents selected from the group consisting of hydroxy, halogen, amino, nitro, cyano, carbonyl, carboxyl, alkoxy, cycloalkyl, heterocyclic, aryl, and heteroaryl,
wherein, alkyl is $C_{1-30}$ alkyl,
alkoxy is $C_{1-30}$ alkoxy,
alkenyl is $C_{2-30}$ alkenyl,
alkynyl is $C_{22-30}$ alkynyl,
cycloalkyl is $C_{3-30}$ cycloalkyl,
aryl is $C_{5-30}$ aryl,
heterocyclic is a heterocyclic having 3 to 30 ring atoms in which one or more ring carbons are each replaced with a heteroatom selected from B, N, O, or S, and
heteroaryl is a heteroaryl having 3 to 30 ring atoms in which one or more ring carbons are each replaced with a heteroatom selected from B, N, O, or S.

In addition, the present invention provides a pharmaceutical composition for preventing or treating obesity, diabetes, or fatty liver, comprising a compound of formula I or a pharmaceutically acceptable salt thereof.

In addition, the present invention provides a method for treating obesity, diabetes, or fatty liver, by administering an effective amount of a compound of formula I or a pharmaceutically acceptable salt thereof to a patient with obesity, diabetes, or fatty liver.

Effect of the Invention

The novel compound of formula I or pharmaceutically acceptable salt thereof of the present invention exhibits excellent GDH activity, and thus can be usefully used as a drug for the prevention or treatment of obesity, diabetes, or fatty liver.

BRIEF DESCRIPTION OF DRAWINGS

FIG. 1 shows the results of measuring the GDH activity for the compound of the present invention.

BEST MODE FOR CARRYING OUT THE INVENTION

The present invention relates to a novel compound of formula I below or a pharmaceutically acceptable salt thereof.

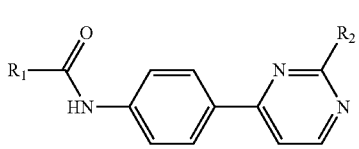

[Formula I]

in which,
$R_1$ is alkyl, alkenyl, alkynyl, cycloalkyl, heterocyclic, aryl, or heteroaryl,
$R_2$ is $NR_3R_4$,
$R_3$ and $R_4$ are independently hydrogen, alkyl, alkenyl, alkynyl, cycloalkyl, heterocyclic, aryl, heteroaryl, alkylcarbonyl, carboxyl, or alkoxycarbonyl, the cycloalkyl, heterocyclic, aryl, or heteroaryl can be substituted with one or more substituents selected from the group consisting of alkyl, alkenyl, alkynyl, hydroxy, halogen, amino, nitro, cyano, carbonyl, carboxyl, alkoxy, aryl, and aryloxy, and
the alkyl, alkenyl or alkynyl can be substituted with one or more substituents selected from the group consisting of hydroxy, halogen, amino, nitro, cyano, carbonyl, carboxyl, alkoxy, cycloalkyl, heterocyclic, aryl, and heteroaryl,
wherein, alkyl is $C_{1-30}$ alkyl,
alkoxy is $C_{1-30}$ alkoxy,
alkenyl is $C_{2-30}$ alkenyl,
alkynyl is $C_{2-30}$ alkynyl,
cycloalkyl is $C_{3-30}$ cycloalkyl,
aryl is $C_{5-30}$ aryl,
heterocyclic is a heterocyclic having 3 to 30 ring atoms in which one or more ring carbons are each replaced with a heteroatom selected from B, N, O, or S, and
heteroaryl is a heteroaryl having 3 to 30 ring atoms in which one or more ring carbons are each replaced with a heteroatom selected from B, N, O, or S.

Preferably, the present invention relates to a compound of formula I below or a pharmaceutically acceptable salt thereof.

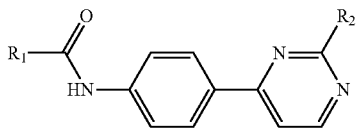

[Formula I]

in which,
$R_1$ is aryl or heteroaryl,
$R_2$ is $NR_3R_4$,
$R_3$ and $R_4$ are independently hydrogen, alkyl, alkenyl, alkenyl, alkylcarbonyl carboxyl, or alkoxycarbonyl, the aryl or heteroaryl can be substituted with one or more substituents selected from the group consisting of alkyl, alkenyl, alkynyl, hydroxy, halogen, amino, nitro, cyano, carbonyl, carboxyl, alkoxy, aryl, and aryloxy, and the alkyl, alkenyl or alkynyl can be substituted with one or more substituents selected from the group consisting of hydroxy, halogen, amino, nitro, cyano, carbonyl, carboxyl, and alkoxy, wherein, alkyl is $C_{1-30}$ alkyl,
alkoxy is $C_{1-30}$ alkoxy,
alkenyl is $C_{2-30}$ alkenyl,
alkynyl is $C_{2-30}$ alkynyl,
aryl is $C_{5-30}$ aryl, and
heteroaryl is a heteroaryl having 3 to 30 ring atoms in which one or more ring carbons are each replaced with a heteroatom selected from B, N, O, or S.

More preferably, the present invention relates to a compound of formula I below or a pharmaceutically acceptable salt thereof.

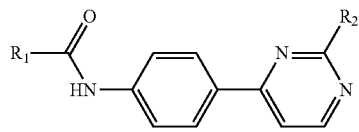
[Formula I]

in which,
$R_1$ is aryl,
$R_2$ is $NR_3R_4$,
$R_3$ and $R_4$ are independently hydrogen or alkoxycarbonyl,
the aryl can be substituted with one or more substituents selected from the group consisting of alkyl, halogen, nitro, alkoxy, aryl, and aryloxy, and
the alkyl can be substituted with one or more halogens, wherein,
alkyl is $C_{1-30}$ alkyl,
alkoxy is $C_{1-30}$ alkoxy, and
aryl is $C_{5-30}$ aryl.

Specifically, the present invention may include the following compounds or pharmaceutically acceptable salts thereof.

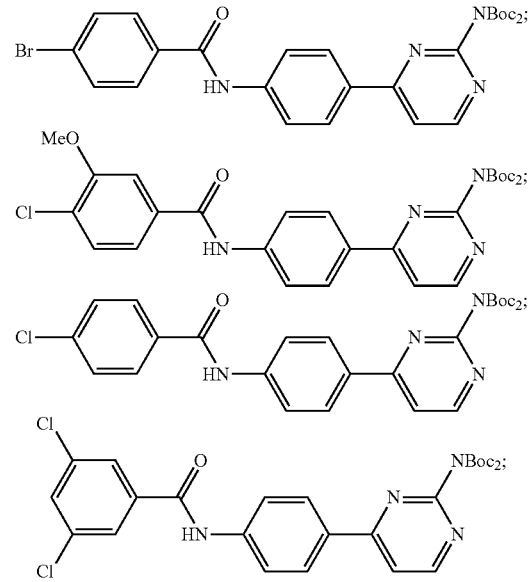

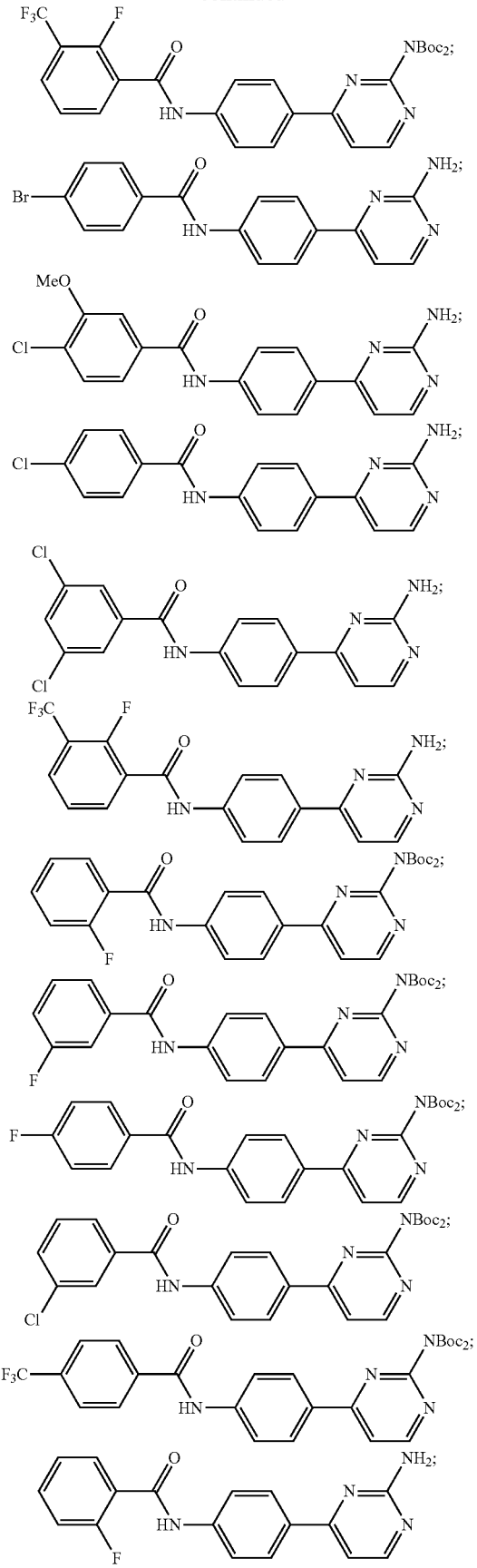

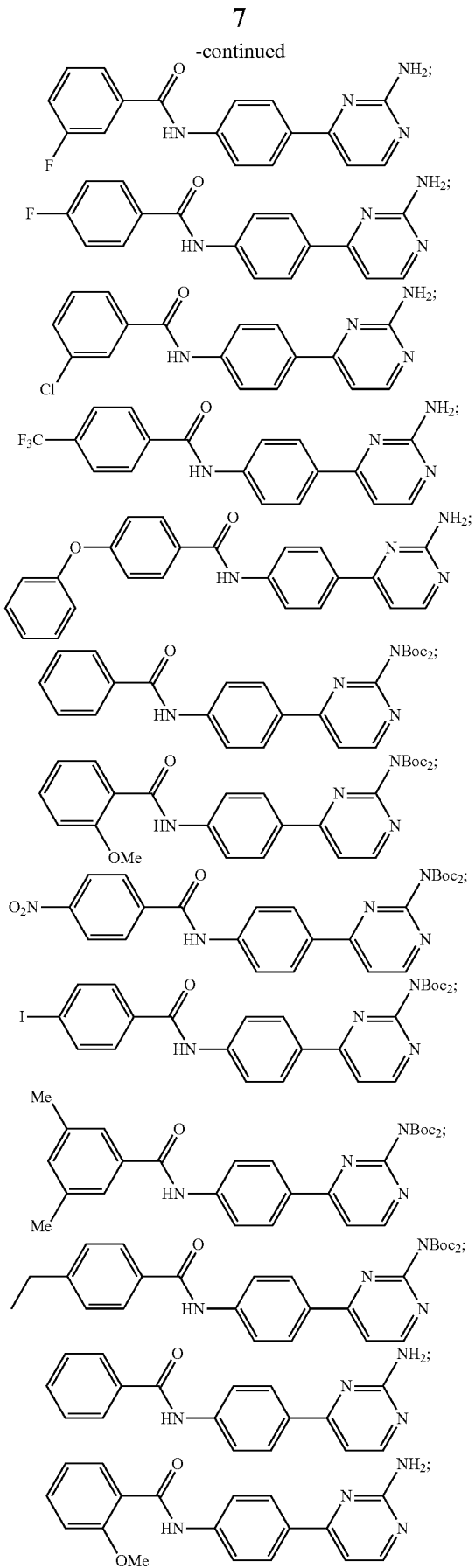

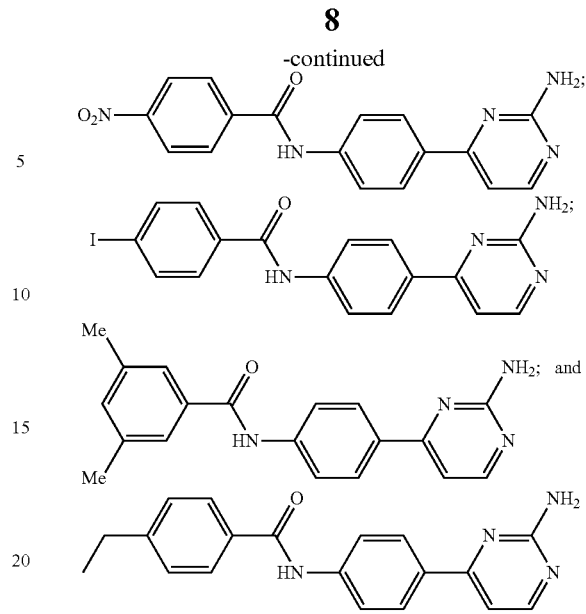

Preferably, the present invention relates to the following compounds or pharmaceutically acceptable salts thereof.

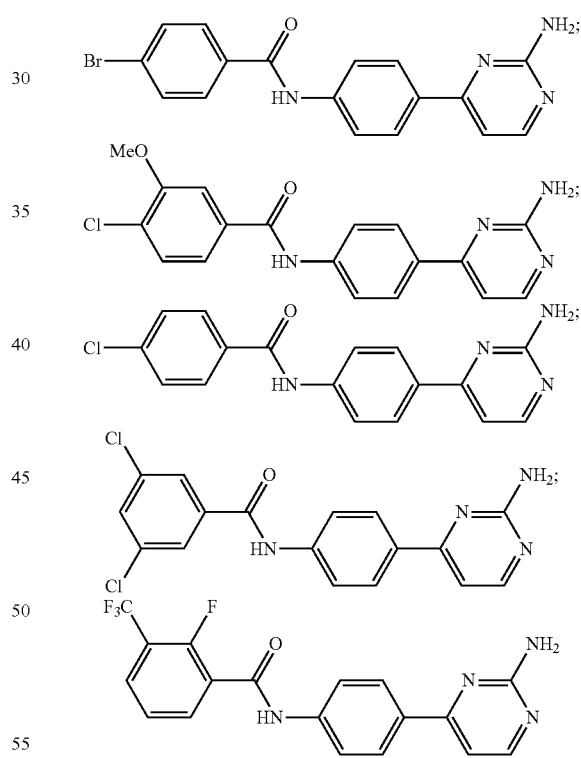

In the present invention, the term "alkyl" refers to a linear or branched hydrocarbon group, which is unsubstituted or substituted with one or more functional groups. Unless otherwise specified, the "alkyl" group preferably contains 1 to 30 carbon atoms. Preferably, the "alkyl" group may be methyl, ethyl, propyl, isopropyl, or butyl, but is not limited thereto.

"Alkoxy" or "alkyloxy" refers to —O-alkyl, which is a functional group to which the alkyl group as defined above is bonded through an oxygen bridge, and is unsubstituted or substituted with one or more functional groups. It preferably contains 1 to 30 carbon atoms.

"Carbonyl" refers to —(C=O)—, which is used alone or in combination with other terms such as "alkoxycarbonyl."

"Alkenyl" refers to a linear, branched or cyclic hydrocarbon group having one or more unsaturated carbon-carbon bonds, which is unsubstituted or substituted with one or more functional groups. Unless otherwise specified, it preferably contains 2 to 30 carbon atoms.

"Alkynyl" refers to a linear or branched hydrocarbon group having one or more carbon-carbon triple bonds, which is unsubstituted or substituted with one or more functional groups. Unless otherwise specified, it preferably contains 2 to 30 carbon atoms.

"Cycloalkyl" refers to a cyclic or polycyclic hydrocarbon group, which is unsubstituted or substituted with one or more functional groups. Unless otherwise specified, it preferably contains 3 to 30 carbon atoms. Preferably, the "cycloalkyl" group may be cyclopropyl, cyclobutyl, cyclopentyl, cyclohexyl, or adamantane, but is not limited thereto.

"Aryl" refers to an aromatic group having 6 to 30 ring carbons, which is unsubstituted or substituted with one or more functional groups. Preferably, the "aryl" group may be phenyl or naphthyl, but is not limited thereto.

"Aryloxy" refers to one including the aryl group, which is optionally substituted, attached to an oxygen atom, and may preferably be phenoxy, but is not limited thereto.

"Heterocyclic" refers to a non-aromatic group in which one or more ring carbons are each replaced with a heteroatom selected from B, N, O, or S, which is unsubstituted or substituted with one or more functional groups. Unless otherwise specified, it preferably contains 3 to 30 ring atoms.

"Heteroaryl" refers to an aromatic group in which one or more ring carbons are each replaced with a heteroatom selected from B, N, O, or S, which is unsubstituted or substituted with one or more functional groups. Unless otherwise specified, it preferably contains 3 to 30 ring atoms.

In addition, the present invention relates to a pharmaceutical composition for preventing or treating obesity, diabetes, or fatty liver, comprising a compound of formula I or a pharmaceutically acceptable salt thereof.

In addition, the present invention relates to a method for treating obesity, diabetes, or fatty liver, comprising administering an effective amount of a compound of formula I or a pharmaceutically acceptable salt thereof to a patient with obesity, diabetes, or fatty liver.

The pharmaceutical acceptable salt may be in the form of an acid addition salt formed by an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid, but is not limited thereto.

In addition, the pharmaceutical composition of the present invention may be prepared as an oral or parenteral preparation. The pharmaceutical preparation for oral or parenteral administration may be unit dosage forms such as, for example, tablets, dispersible tablets, coated tablets, effervescent tablets, capsules, suspendible powders, suspensions, suppositories, or ampoules. They are prepared by known methods, for example, by processes such as mixing, granulation, coating or freeze drying.

The pharmaceutical preparation for oral administration may be prepared by combining an active ingredient with solid carriers, granulating the obtained mixture if necessary, and processing the mixture or granules, if necessary, after the addition of suitable additives to obtain tablets or coated tablet cores.

The suitable carriers may include sugar (for example, lactose, sucrose, mannitol or sorbitol), cellulose, calcium phosphate (for example, tricalcium phosphate or calcium hydrogen phosphate) or the like as a filler; may include starch (for example, corn, wheat, rice or potato starch), gelatin, tragacanth, methylcellulose, polyvinylpyrrolidone or the like as a binder; and may include starch, polyvinylpyrrolidone, agar, alginic acid or sodium alginate or the like as a disintegrant.

The additive may include salicylic acid, talc, stearic acid, magnesium stearate, calcium stearate, polyethylene glycol or the like as a lubricant.

For parenteral administration, it may be an aqueous solution of the active ingredient in a water-soluble form, for example, in a water-soluble salt form.

The dosage of the active ingredient may be determined according to various factors such as the activity and duration of action of the active ingredient, the severity of the disease to be treated or its symptoms, the method of administration, the species, sex, age and body weight of the warm-blooded animal and individual condition of the warm-blooded animal.

Specific compounds of formula I of the present invention were prepared in the same manner as in Schemes 1 to 6 below, and the specific compounds are shown in Table 1.

TABLE 1

| Compound No. | Structure | Compound name |
|---|---|---|
| 1 | [structure: 4-bromobenzamide linked via HN–C(=O) to a phenyl-pyrimidine bearing NBoc₂] | N-(4-(2-(N,N-di-t-butyloxycarbonyl)aminopyrimidin-4-yl)phenyl)-4-bromobenzamide |
| 2 | [structure: 4-chloro-3-methoxybenzamide linked via HN–C(=O) to a phenyl-pyrimidine bearing NBoc₂] | N-(4-(2-(N,N-di-t-butyloxycarbonyl)aminopyrimidin-4-yl)phenyl)-4-chloro-3-methoxybenzamide |

TABLE 1-continued

| Compound No. | Structure | Compound name |
|---|---|---|
| 3 | 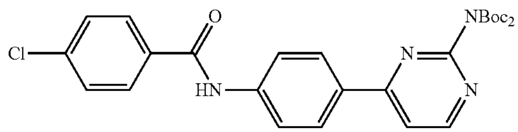 | N-(4-(2-(N,N-di-t-butyloxy-carbonyl)aminopyrimidin-4-yl)phenyl)-4-chloro-benzamide |
| 4 | 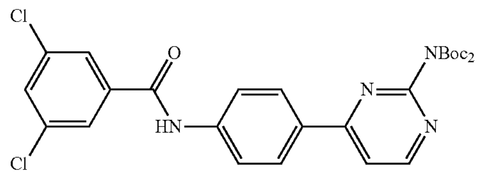 | N-(4-(2-(N,N-di-t-butyloxy-carbonyl)aminopyrimidin-4-yl)phenyl)-3,5-dichloro-benzamide |
| 5 | 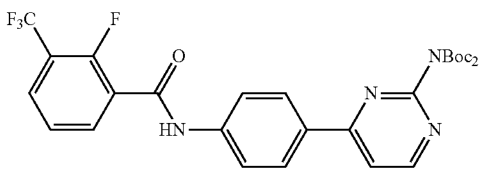 | N-(4-(2-(N,N-di-t-butyloxy-carbonyl)aminopyrimidin-4-yl)phenyl)-2-fluoro-3-(trifluoromethyl)benzamide |
| 6 | 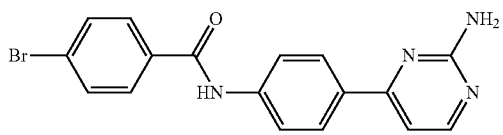 | N-(4-(2-aminopyrimidin-4-yl)phenyl)-4-bromo-benzamide |
| 7 | 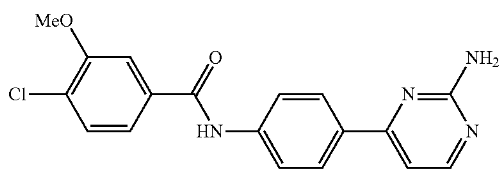 [SMILES: COc1cc(C(=O)Nc2ccc(-c3ccnc(N)n3)cc2)ccc1Cl] | N-(4-(2-aminopyrimidin-4-yl)phenyl)-4-chloro-3-methoxybenzamide |
| 8 | 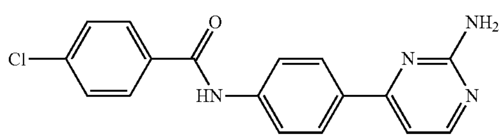 [SMILES: Nc1nccc(-c2ccc(NC(=O)c3ccc(Cl)cc3)cc2)n1] | N-(4-(2-aminopyrimidin-4-yl)phenyl)-4-chloro-benzamide |
| 9 | 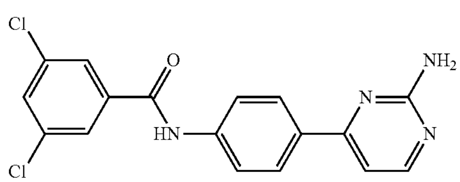 [SMILES: Nc1nccc(-c2ccc(NC(=O)c3cc(Cl)cc(Cl)c3)cc2)n1] | N-(4-(2-aminopyrimidin-4-yl)phenyl)-3,5-dichloro-benzamide |
| 10 | 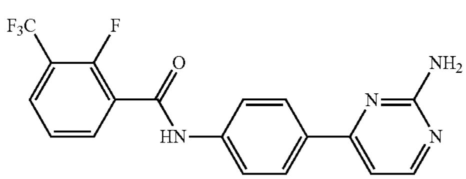 [SMILES: Nc1nccc(-c2ccc(NC(=O)c3cccc(C(F)(F)F)c3F)cc2)n1] | N-(4-(2-aminopyrimidin-4-yl)phenyl)-2-fluoro-3-(trifluoromethyl)benzamide |
| 11 | 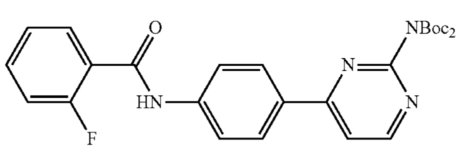 | N-(4-(2-(N,N-di-t-butyloxy-carbonyl)aminopyrimidin-4-yl)phenyl)-2-fluoro-benzamide |

TABLE 1-continued

| Compound No. | Structure | Compound name |
|---|---|---|
| 12 | 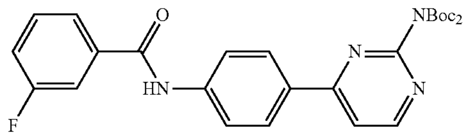 | N-(4-(2-(N,N-di-t-butyloxy-carbonyl)aminopyrimidin-4-yl)phenyl)-3-fluoro-benzamide |
| 13 | 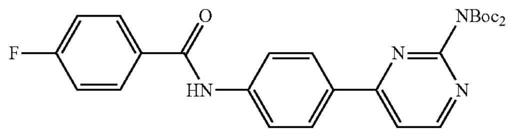 | N-(4-(2-(N,N-di-t-butyloxy-carbonyl)aminopyrimidin-4-yl)phenyl)-4-fluoro-benzamide |
| 14 | 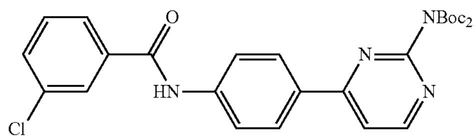 | N-(4-(2-(N,N-di-t-butyloxy-carbonyl)aminopyrimidin-4-yl)phenyl)-3-chloro-benzamide |
| 15 | 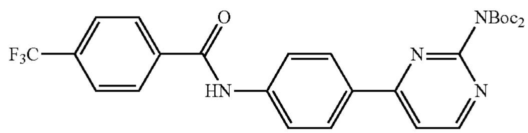 | N-(4-(2-(N,N-di-t-butyloxy-carbonyl)aminopyrimidin-4-yl)phenyl)-4-(trifluoro-methyl)benzamide |
| 16 | 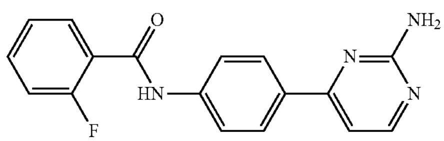 [SMILES: Nc1nccc(-c2ccc(NC(=O)c3ccccc3F)cc2)n1] | N-(4-(2-aminopyrimidin-4-yl)phenyl)-2-fluoro-benzamide |
| 17 | 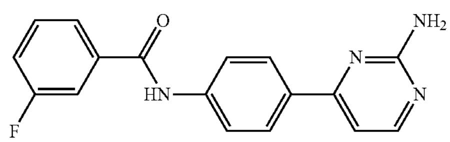 [SMILES: Nc1nccc(-c2ccc(NC(=O)c3cccc(F)c3)cc2)n1] | N-(4-(2-aminopyrimidin-4-yl)phenyl)-3-fluoro-benzamide |
| 18 | 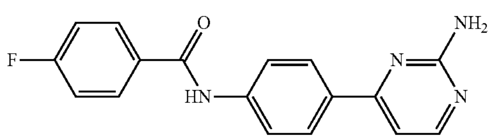 | N-(4-(2-aminopyrimidin-4-yl)phenyl)-4-fluoro-benzamide |
| 19 | 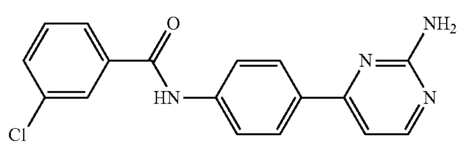 [SMILES: Nc1nccc(-c2ccc(NC(=O)c3cccc(Cl)c3)cc2)n1] | N-(4-(2-aminopyrimidin-4-yl)phenyl)-3-chloro-benzamide |
| 20 | 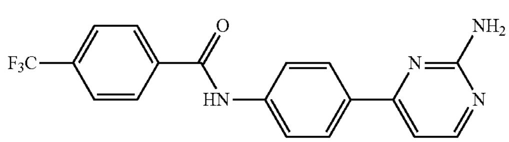 | N-(4-(2-aminopyrimidin-4-yl)phenyl)-4-(trifluoro-methyl)benzamide |
| 21 | 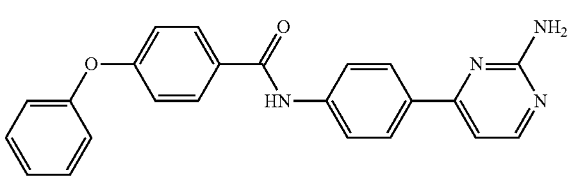 [SMILES: Nc1nccc(-c2ccc(NC(=O)c3ccc(Oc4ccccc4)cc3)cc2)n1] | N-(4-(2-aminopyrimidin-4-yl)phenyl)-4-phenoxy-benzamide |

TABLE 1-continued

| Compound No. | Structure | Compound name |
|---|---|---|
| 22 | 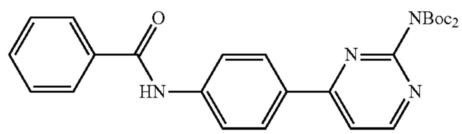 | N-(4-(2-(N,N-di-t-butyloxy-carbonyl)aminopyrimidin-4-yl)phenyl)benzamide |
| 23 | 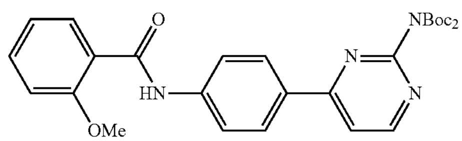 | N-(4-(2-(N,N-di-t-butyloxy-carbonyl)aminopyrimidin-4-yl)phenyl)-2-methoxy-benzamide |
| 24 | 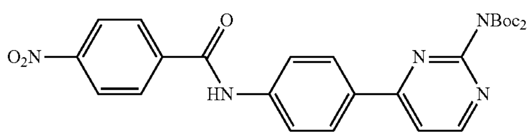 | N-(4-(2-(N,N-di-t-butyloxy-carbonyl)aminopyrimidin-4-yl)phenyl)-4-nitrobenz-amide |
| 25 | 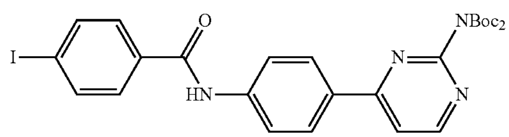 | N-(4-(2-(N,N-di-t-butyloxy-carbonyl)aminopyrimidin-4-yl)phenyl)-4-iodobenzamide |
| 26 | 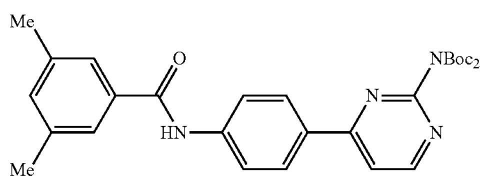 | N-(4-(2-(N,N-di-t-butyloxy-carbonyl)aminopyrimidin-4-yl)phenyl)-3,5-dimethyl-benzamide |
| 27 | 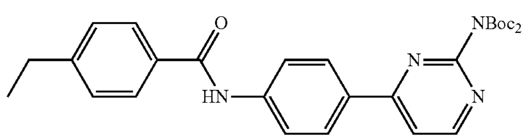 | N-(4-(2-(N,N-di-t-butyloxy-carbonyl)aminopyrimidin-4-yl)phenyl)-4-ethylbenzamide |
| 28 | 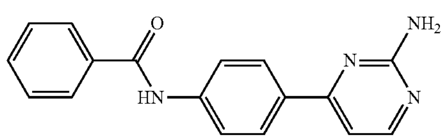 [SMILES: Nc1nccc(-c2ccc(NC(=O)c3ccccc3)cc2)n1] | N-(4-(2-aminopyrimidin-4-yl)phenyl)benzamide |
| 29 | 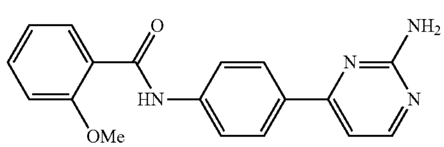 | N-(4-(2-aminopyrimidin-4-yl)phenyl)-2-methoxybenz-amide |
| 30 | 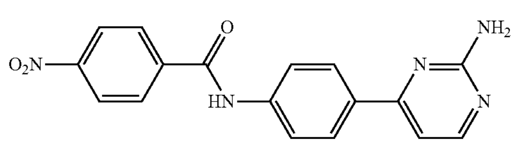 | N-(4-(2-aminopyrimidin-4-yl)phenyl)-4-nitrobenzamide |
| 31 | 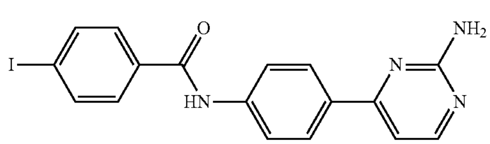 [SMILES: Nc1nccc(-c2ccc(NC(=O)c3ccc(I)cc3)cc2)n1] | N-(4-(2-aminopyrimidin-4-yl)phenyl)-4-iodobenzamide |

TABLE 1-continued

| Compound No. | Structure | Compound name |
|---|---|---|
| 32 | 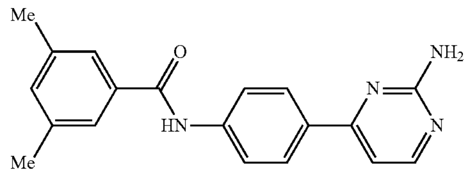 [SMILES: Cc1cc(C)cc(C(=O)Nc2ccc(-c3ccnc(N)n3)cc2)c1] | N-(4-(2-aminopyrimidin-4-yl)phenyl)-3,5-dimethyl-benzamide |
| 33 | 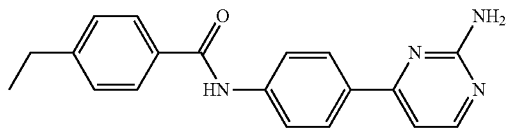 [SMILES: CCc1ccc(C(=O)Nc2ccc(-c3ccnc(N)n3)cc2)cc1] | N-(4-(2-aminopyrimidin-4-yl)phenyl)-4-ethylbenzamide |

[Scheme 1]

Compounds 1 to 5 in Table 1 above were prepared by the same preparation method as in Scheme 1 below,

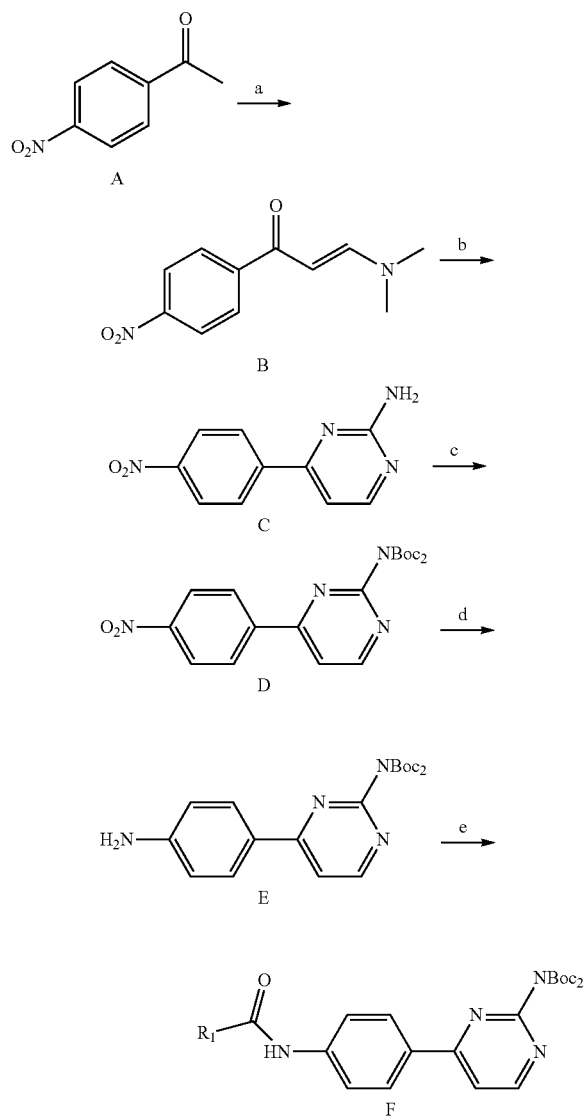

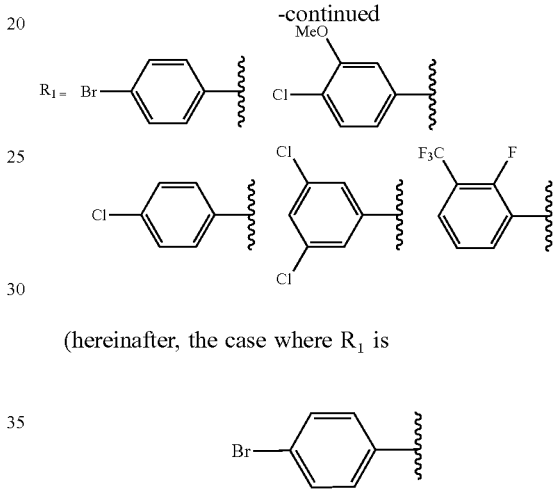

(hereinafter, the case where $R_1$ is is described as a representative)

Step a: Preparation of (E)-3-(dimethyl amino)-1-(4-nitrophenyl)prop-2-en-1-one

4'-nitroacetophenone (3.3 g, 20 mmol) was dissolved in toluene (100 mL), and then dimethylformamide dimethyl acetal (2.3 g, 20 mmol) was added, and refluxed for 12 hours. Toluene was distilled off, and the product was pulverized with petroleum ether. The resulting solid was filtered and washed with cold petroleum ether to obtain the pure product (3.5 g, 81%) as a tan solid.

Step b: Preparation of 4-(4-nitrophenyl)pyrimidin-2-amine

To a solution in which sodium hydroxide (539 mg, 13.4 mmol) was dissolved in ethanol (30 mL) was added guanidine hydrochloride (1.2 g, 13.4 mmol), and stirred for 30 minutes, and then a solution in which intermediate 2 (2.7 g, 12.2 mmol) was dissolved in ethanol (8 mL) was added at ambient temperature. The reaction was stirred at 40° C. for 12 hours. After completion of the reaction, the reaction was diluted with water and extracted with ethyl acetate to obtain Compound C (1.5 g, 57%).

Step c: Preparation of N,N-di-t-butyloxycarbonyl-4-(4-nitrophenyl)pyrimidin-2-amine A solution in which Compound C (1.9 g, 8.8 mmol) was dissolved in dichloromethane (50 mL) was cooled to 0° C., and then triethylamine (2.4 mL, 17.7 mmol), di-tert-butyl dicarbonate (3.8 g, 17.7 mmol) and 4-dimethylaminopyridine (2.1 g, 17.7 mmol) were added. The reaction was stirred at ambient temperature for 12 hours and diluted with dichloromethane. The organic layer was cleaned with a saturated sodium hydrogen carbonate solution and brine solution and dried over anhydrous magnesium sulfate. The solvent was concentrated to obtain the unpurified product, which was purified using column chromatography (hexane:ethyl acetate=2:1) to obtain Compound D (1.1 g, 41%).

Step d: Preparation of N,N-di-t-butyloxycarbonyl-4-(4-aminophenyl)pyrimidin-2-amine To a solution in which Compound D (1.1 g, 3.6 mmol) was dissolved in tetrahydrofuran (3 mL) and methanol (18 mL) was added 10% palladium carbon (116 mg) under vacuum, and then hydrogen gas was injected with a balloon. The reaction mixture was stirred at room temperature for about 12 hours. After completion of the reaction, the reaction mixture was filtered through a pad of Celite, and the filtrate was concentrated and purified using column chromatography (hexane:ethyl acetate=1:1) to obtain Compound E (960 mg, 91%).

Step e: Preparation of N-(4-(2-(N,N-di-t-butyloxycarbonyl)aminopyrimidin-4-yl)phenyl)-4-bromobenzamide Compound E (50 mg, 0.1 mmol) of Step d above, 1-ethyl-3-(3-dimethylaminopropyl)carbodimide (50 mg, 0.3 mmol), 1-hydroxybenzotriazole hydrate (40 mg, 0.3 mmol), and 4-(dimethylamino)pyridine (9 mg, 0.1 mmol) were dissolved in dichloromethane (0.5 mL), and then 4-bromobenzoic acid (52 mL, 0.3 mmol) was added, and then stirred at ambient temperature for 12 hours. The mixture was diluted with an ammonium chloride solution. The organic layer was dried over anhydrous magnesium sulfate, and the solvent was concentrated under vacuum and purified using column chromatography (hexane:ethyl acetate=1:1).

[Scheme 2]

Compounds 6 to 10 in Table 1 above were prepared by the same preparation method as in Scheme 2 below.

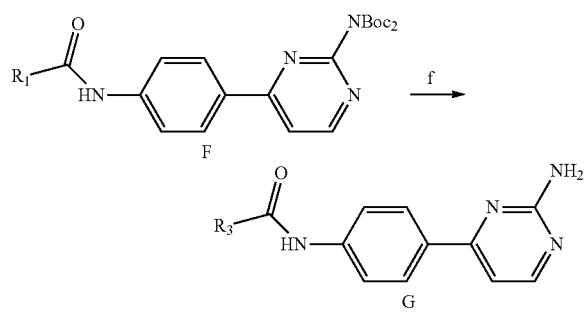

Step f: Preparation of N-(4-(2-aminopyrimidin-4-yl)phenyl)-4-bromobenzamide

4-Normal hydrogen chloride (0.7 mL) dissolved in dioxane was added to Compound F (42 mg, 0.1 mmol) of Step e above, and the mixture was stirred at room temperature for 12 hours. The solvent was concentrated by evaporation under vacuum and then recrystallized.

[Scheme 3]

Compounds 11 to 15 in Table 1 above were prepared by the same preparation method as in Scheme 3 below.

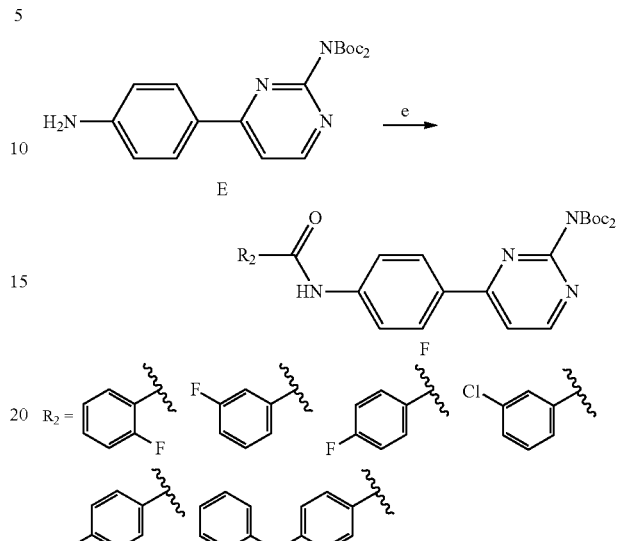

(hereinafter, the case where $R_2$ is

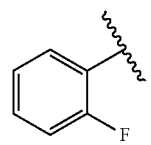 [SMILES: *c1ccccc1F]

is described as a representative)

Step e: Preparation of N-(4-(2-(N,N-di-t-butyloxycarbonyl)aminopyrimidin-4-yl)phenyl)-2-fluorobenzamide Compound E (100 mg, 0.5 mmol), 1-ethyl-3-(3-dimethylaminopropyl)carbodiimide (100 mg, 1.3 mmol), and 4-(dimethylamino)pyridine (80 mg, 2.5 mmol) were dissolved in dimethylformamide (2 mL), and then 2-fluorobenzoic acid (72 mg, 1.3 mmol) was added, and then stirred at ambient temperature for 12 hours. The mixture was diluted with an ammonium chloride solution. The organic layer was dried over anhydrous magnesium sulfate, and the solvent was concentrated under vacuum and purified using column chromatography (hexane:ethyl acetate=1:1).

[Scheme 4]

Compounds 16 to 21 in Table 1 above were prepared by the same preparation method as in Scheme 4 below

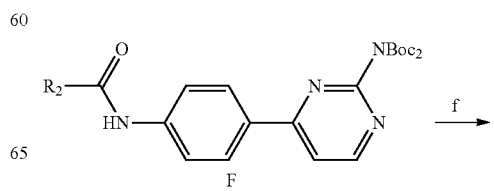

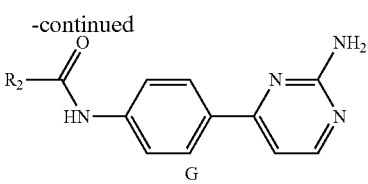

Step f: Preparation of N-(4-(2-aminopyrimidin-4-yl)phenyl)-2-fluorobenzamide

4-Normal hydrogen chloride (1.3 mL) dissolved in dioxane was added to Compound F (67 mg, 0.1 mmol), and the mixture was stirred at room temperature for 12 hours. The solvent was concentrated by evaporation under vacuum and then recrystallized.

[Scheme 5]

Compounds 22 to 27 in Table 1 above were prepared by the same preparation method as in Scheme 5 below

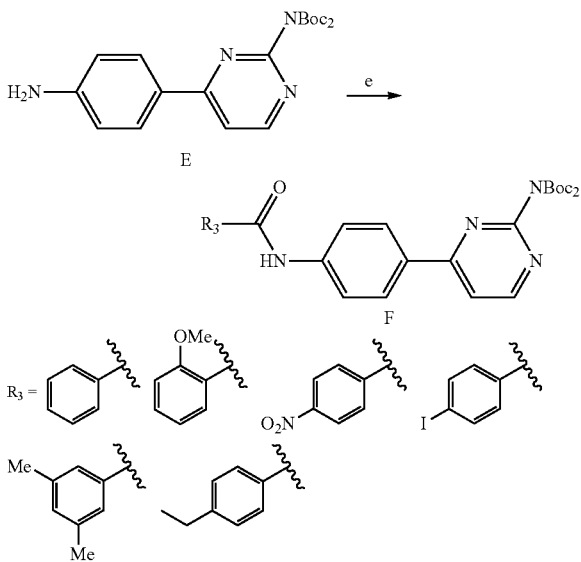

(hereinafter, the case where R₃ is

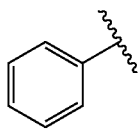 [SMILES: *c1ccccc1]

is described as a representative)

Step e: Preparation of N-(4-(2-(N,N-di-t-butyloxycarbonyl)aminopyrimidin-4-yl)phenyl)benzamide Compound E (100 mg, 0.3 mmol) and 4-(dimethylamino)pyridine (79 mg, 0.6 mmol) were dissolved in dichloromethane (1 mL), and then benzoyl chloride (0.1 mL, 0.8 mmol) was added, and then stirred at ambient temperature for 12 hours. The mixture was diluted with an ammonium chloride solution. The organic layer was dried over anhydrous magnesium sulfate, and the solvent was concentrated under vacuum and purified using column chromatography (hexane:ethyl acetate=1:1).

[Scheme 6]

Compounds 28 to 33 in Table 1 above were prepared by the same preparation method as in Scheme 6 below

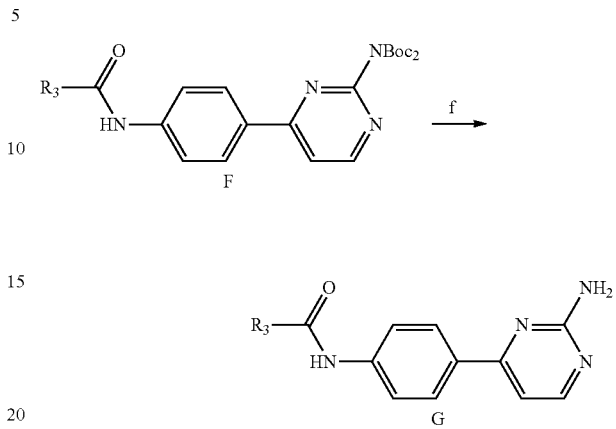

Step f: Preparation of N-(4-(2-aminopyrimidin-4-yl)phenyl)benzamide

4-Normal hydrogen chloride (0.6 mL) dissolved in dioxane was added to Compound F (30 mg, 0.1 mmol) of Step e above, and the mixture was stirred at room temperature for 12 hours. The solvent was concentrated by evaporation under vacuum and then recrystallized.

Hereinafter, the present invention will be described in more detail through the following examples, and the present invention is not limited by these examples.

Example 1

Compound B: (E)-3-(dimethylamino)-1-(4-nitrophenyl)prop-2-en-1-one

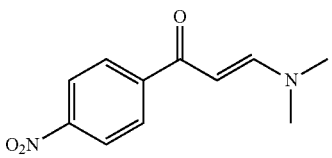

4'-nitroacetophenone (3.3 g, 20 mmol) was dissolved in toluene (100 mL), and then dimethylformamide dimethyl acetal (2.3 g, 20 mmol) was added, and the reaction was refluxed for 12 hours. Toluene was distilled off, and the product was pulverized with petroleum ether. The resulting solid was filtered and washed with cold petroleum ether to obtain the pure product (3.5 g, 81%) as a tan solid.

$^1$H NMR (600 MHz, DMSO-$d_6$) δ 8.26 (d, J=8.8 Hz, 2H), 8.11 (d, J=8.8 Hz, 2H), 7.80 (d, J=12.1 Hz, 1H), 5.87 (d, J=12.1 Hz, 1H), 3.18 (s, 3H), 2.96 (s, 3H), $^{13}$C NMR (150 MHz, DMSO-$d_6$) δ 155.7, 149.0, 146.2, 128.9, 123.9, 45.2, 37.8.

Example 2

Compound C: 4(4-nitrophenyl)pyrimidin-2-amine

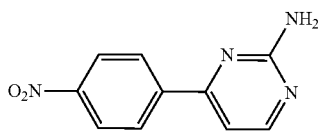

To a solution in which sodium hydroxide (539 mg, 13.4 mmol) was dissolved in ethanol (30 mL) was added guanidine hydrochloride (1.2 g, 13.4 mmol), and stirred for 30 minutes, and then a solution in which Intermediate 2 (2.7 g, 12.2 mmol) was dissolved in ethanol (8 mL) was added at ambient temperature. The reaction was stirred at 40° C. for 12 hours. After completion of the reaction, the reaction was diluted with water and extracted with ethyl acetate to obtain Compound C (1.5 g, 57%).

$^1$H NMR (600 MHz, DMSO-$d_6$) δ 8.40 (d, J=5.1 Hz, 1H), 8.34-8.28 (m, 4H), 7.23 (d, J=5.1 Hz, 1H), 6.85 (s, 2H), $^{13}$C NMR (150 MHz, DMSO-$d_6$) δ 164.3, 161.8, 160.3, 149.0, 143.5, 128.4, 124.3, 107.1.

Example 3

Compound D: N,N-di-t-butyloxycarbonyl-4-(4-nitrophenyl)pyrimidin-2-amine

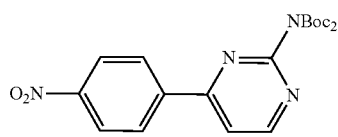

A solution in which Compound C (1.9 g, 8.8 mmol) was dissolved in dichloromethane (50 mL) was cooled to 0° C., and then triethylamine (2.4 mL, 17.7 mmol), di-tert-butyl dicarbonate (3.8 g, 17.7 mmol) and 4-dimethylaminopyridine (2.1 g, 17.7 mmol) were added. The reaction was stirred at ambient temperature for 12 hours and diluted with dichloromethane. The organic layer was cleaned with a saturated sodium hydrogen carbonate solution and brine solution and dried over anhydrous magnesium sulfate. The solvent was concentrated to obtain the unpurified product, which was purified using column chromatography (hexane:ethyl acetate=2:1) to obtain Compound D (1.1 g, 41%).

$^1$H NMR (600 MHz, DMSO-$d_6$) δ 9.05 (d, J=5.2 Hz, 1H), 8.48-8.45 (m, 2H), 8.44-8.41 (m, 2H), 8.23 (d, J=5.3 Hz, 1H), 1.42 (s, 9H), $^{13}$C NMR (150 MHz, DMSO-$d_6$) δ 163.1, 161.3, 158.7, 150.8, 149.7, 141.3, 128.9, 124.8, 116.6, 83.6, 27.8.

Example 4

Compound E: N,N-di-t-butyloxycarbonyl-4-(4-aminophenyl)pyridimin-2-amine

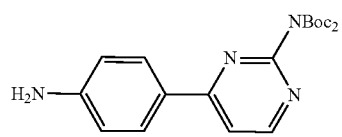

To a solution in which Compound D (1.1 g, 3.6 mmol) was dissolved in tetrahydrofuran (3 mL) and methanol (18 mL) was added 10% palladium carbon (116 mg) under vacuum, and then hydrogen gas was injected with a balloon. The reaction mixture was stirred at room temperature for about 12 hours. After completion of the reaction, the reaction mixture was filtered through a pad of Celite, and the filtrate was concentrated and purified using column chromatography (hexane:ethyl acetate-=1:1) to obtain Compound E (960 mg, 91%).

$^1$H NMR (600 MHz, DMSO-$d_6$) δ 8.62 (d, J=5.4 Hz, 1H), 7.90 (d, J=8.7 Hz, 2H), 7.73 (d, J=5.5 Hz, 1.14), 6.64 (d, J=8.7 Hz, 2H), 5.89 (s, 18H), 1.38 (s, 18H), $^{13}$C NMR (150 MHz, DMSO-$d_6$) δ 165.5, 159.0, 158.4, 153.0, 151.1, 129.1, 122.0, 114.0, 113.1, 83.1, 27.9.

Example 5

Compound 1 below was prepared by the following method.

Compound 1: N-(4-(2-(N,N-di-t-butyloxycarbonyl) aminopyrimidin-4-yl)phenyl)-4-bromobenzamide

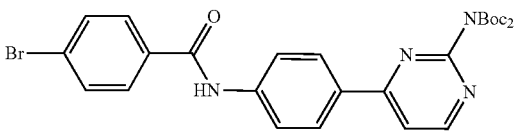

Compound E (50 mg, 0.1 mmol), 1-ethyl-3-(3-dimethylaminopropyl)carbodimide (50 mg, 0.3 mmol), 1-hydroxybenzotriazole hydrate (40 mg, 0.3 mmol), and 4-(dimethylamino)pyridine (9 mg, 0.1 mmol) were dissolved in dichloromethane (0.5 mL), and then 4-bromobenzoic acid (52 mL, 0.3 mmol) was added, and then stirred at ambient temperature for 12 hours. The mixture was diluted with an ammonium chloride solution. The organic layer was dried over anhydrous magnesium sulfate, and the solvent was concentrated under vacuum and purified using column chromatography (hexane:ethyl acetate=1:1).

$^1$H NMR (600 MHz, Chloroform-d) δ 8.6 (dd, J=5.3, 2.2 Hz, 1H), 8.5 (d, J=8.7 Hz, 1H), 8.0-7.9 (m, 2H), 7.8-7.8 (m, 2H), 7.7 (dd, J=8.6, 1.8 Hz, 2H), 7.6 (dd, J=8.4, 1.5 Hz, 2H), 7.4 (dd, J=5.4, 2.1 Hz, 1H), 1.5 (s, 18H), $^{13}$C NMR (151 MHz, CDCl$_3$) δ 165.0, 165.0, 158.8, 158.6, 151.3, 141.1, 133.4, 131.9, 130.9, 129.0, 128.9, 128.0, 126.8, 120.1, 113.9, 83.7, 27.9, 27.9.

Example 6

Compound 2 below was prepared in the same manner as in Example 5 above.

Compound 2: N-(4-(2-1N,N-di-t-butyloxycarbonyl)aminopyrimidin-4-phenyl)-4-chloro-3-methoxybenzamide

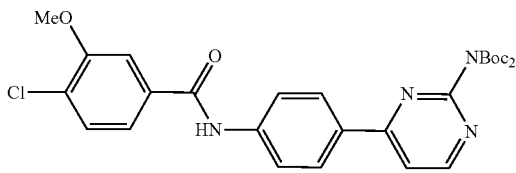

$^1$H NMR (600 MHz, Chloroform-d) δ 8.7 (d, J=5.3 Hz, 1H), 8.0 (d, J=8.8 Hz, 2H), 7.7 (d, J=8.8 Hz, 2H), 7.6 (d, J=1.8 Hz, 1H), 7.5 (d, J=5.3 Hz, 1H), 7.5-7.4 (m, 2H), 4.0 (s, 3H), 1.5 (s, 19H), $^{13}$C NMR (151 MHz, CDCl$_3$) δ 165.1, 165.1, 158.8, 158.6, 155.4, 154.9, 151.3, 150.9, 134.3, 130.9, 130.2, 128.0, 126.6, 123.1, 120.2, 113.9, 111.5, 83.7, 56.4, 27.9.

Example 7

Compound 3 below was prepared in the same manner as in Example 5 above.

Compound 3: N-(4-(2-(N,N-di-t-butyloxycarbonyl)aminopyrimidin-4-yl)phenyl)-4-chlorobenzamide

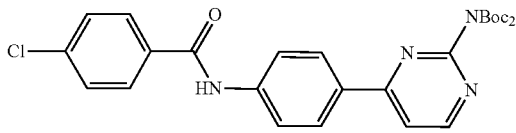

$^1$H NMR (600 MHz, Chloroform-d) δ 8.6 (d, J=5.3 Hz, 1H), 8.4 (s, 1H), 8.0 (d, J=8.7 Hz, 2H), 7.9 (d, J=8.6 Hz, 2H), 7.7 (d, J=8.8 Hz, 2H), 7.5-7.4 (m, 3H), 1.5 (s, 18H), $^{13}$C NMR (151 MHz, CDCl$_3$) δ 165.0, 164.8, 158.9, 158.6, 151.2, 141.0, 138.3, 132.9, 131.1, 129.0, 128.8, 128.1, 120.1, 113.9, 83.6, 27.9.

Example 8

Compound 4 below was prepared in the same manner as in Example 5 above.

Compound 4: N-(4-(2-(N,N-di-t-butyloxycarbonyl)aminopyrimidin-4-yl)phenyl)-3,5-dichlorobenzamide

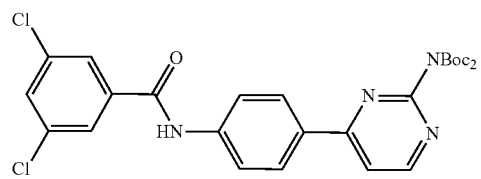

$^1$H NMR (600 MHz, Chloroform-d) δ 8.7 (t, J=2.7 Hz, 2H), 8.0-7.9 (m, 3H), 7.8 (d, J=1.9 Hz, 2H), 7.7-7.7 (m, 2H), 7.5 (t, J=1.9 Hz, 1H), 7.5 (t, J=4.6 Hz, 1H), 1.5 (d, J=1.2 Hz, 19H), $^{13}$C NMR (151 MHz, CDCl$_3$) δ 165.1, 163.4, 158.8, 158.5, 151.3, 137.4, 135.5, 131.8, 128.5, 128.1, 126.1, 120.2, 113.9, 83.8, 27.9.

Example 9

Compound 5 below was prepared in the same manner as in Example 5 above.

Compound 5: N-(4-(2-(N,N-di-t-butyloxycarbonyl)aminopyrimidin-4-yl) 2-fluoro-3-(trifluoromethyl)benzamide

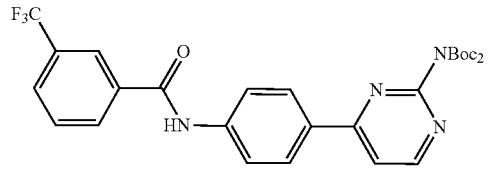

$^1$H NMR (600 MHz, Chloroform-d) δ 8.8 (d, J=5.2 Hz, 1H), 8.6 (d, J=12.7 Hz, 1H), 8.4 (t, J=7.6 Hz, 1H), 8.1 (d, J=8.5 Hz, 2H), 7.8 (dd, J=8.5, 6.7 Hz, 3H), 7.6 (d, J=5.3 Hz, 1H), 7.5 (t, J=7.8 Hz, 1H), 1.5 (s, 18H), $^{13}$C NMR (151 MHz, CDCl$_3$) δ 164.8, 160.1, 159.0, 158.9, 156.6, 150.9, 140.2, 136.2, 132.2, 130.9, 128.3, 125.1, 125.1, 123.0, 122.9, 122.9, 121.2, 120.5, 113.8, 83.3, 27.9.

Example 10

Compound 6 below was prepared as follows.

Compound 6: N-(4-(2-aminopyrimidin-4-yl)phenyl)-4-bromobenzamide

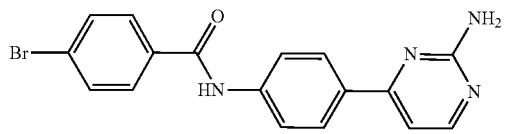 [SMILES: Nc1nccc(-c2ccc(NC(=O)c3ccc(Br)cc3)cc2)n1]

4-Normal hydrogen chloride (0.7 mL) dissolved in dioxane was added to Compound F (42 mg, 0.1 mmol) of Scheme 2 above, and the mixture was stirred at room temperature for 12 hours. The solvent was concentrated by evaporation under vacuum and then recrystallized.

$^1$H NMR (600 MHz, DMSO-d$_6$) δ 10.9 (s, 1H), 8.5 (d, J=6.6 Hz, 1H), 8.3-8.3 (m, 2H), 8.1-8.1 (m, 2H), 8.0-8.0 (m, 2H), 7.8-7.8 (m, 2H), 7.6 (d, J=6.6 Hz, 1H), $^{13}$C NMR (151 MHz, CDCl$_3$) δ 170.3, 161.1, 149.1, 138.7, 136.7, 135.3, 135.3, 135.3, 134.5, 134.4, 134.1, 131.0, 125.4, 125.3, 119.1, 110.7, 110.6, 68.0.

Example 11

Compound 7 below was prepared in the same manner as in Example 10 above.

Compound 7: N-(4-(2-aminopyrimidin-4-yl)phenyl)-4-chloro-3-methoxybenzamide

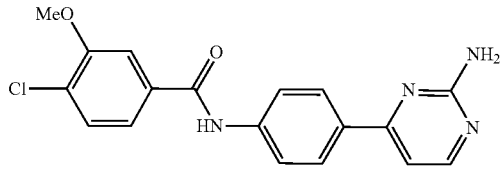 [SMILES: COc1cc(C(=O)Nc2ccc(-c3ccnc(N)n3)cc2)ccc1Cl]

$^1$H NMR (600 MHz, DMSO-d$_6$) δ 10.8 (s, 1H), 8.4 (d, J=6.2 Hz, 1H), 8.2 (d, J=8.4 Hz, 2H), 8.0 (d, J=8.5 Hz, 2H), 7.7 (s, 1H), 7.6 (s, 2H), 7.5 (d, J=6.2 Hz, 1H), 4.0 (s, 3H), $^{13}$C NMR (151 MHz, CDCl$_3$) δ 170.2, 161.6, 159.6, 148.9, 139.7, 135.1, 134.3, 134.3, 130.1, 126.2, 125.5, 125.4, 119.9, 117.3, 110.7, 61.6.

Example 12

Compound 8 below was prepared in the same manner as in Example 10 above.

Compound 8: N-(4-(2-aminopyrimidin-4-yl)phenyl)-4-chlorobenzamide

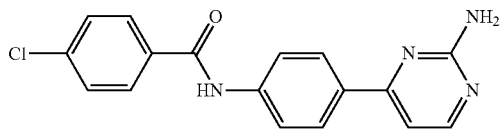 [SMILES: Nc1nccc(-c2ccc(NC(=O)c3ccc(Cl)cc3)cc2)n1]

$^1$H NMR (600 MHz, DMSO-d$_6$) δ 10.8 (s, 1H), 8.5 (d, J=6.5 Hz, 1.1-1), 8.3-8.2 (m, 2H), 8.1-8.0 (m, 4H), 7.7-7.6 (m, 2H), 7.5 (d, J=6.5 Hz, 1H), $^{13}$C NMR (151 MHz, DMSO) δ 170.8, 165.4, 144.1, 137.3, 133.6, 130.3, 129.6, 129.0, 120.6, 105.9, 63.3, 60.2, 55.4, 21.2, 14.6.

Example 13

Compound 9 below was prepared in the same manner as in Example 10 above.

Compound 9: N-(4-(2-aminopyrimidin-4-yl)phenyl)-3,5-dichlorobenzamide

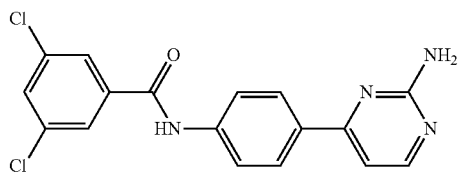

$^1$H NMR (600 MHz, DMSO-d$_6$) δ 11.0 (s, 1H), 8.5 (d, J=6.6 Hz, 1H), 8.3-8.3 (m, 2H), 8.1-8.0 (m, 4H), 7.9 (t, J=1.9 Hz, 1H), 7.6 (d, J=6.6 Hz, 1H), 3.6 (s, 2H), $^{13}$C NMR (151 MHz, DMSO) δ 163.6, 156.5, 143.9, 137.9, 134.8, 131.7, 129.6, 127.2, 120.7, 105.9, 66.8.

Example 14

Compound 10 below was prepared in the same manner as in Example 10 above.

Compound 10: N-(4-(2-aminopyrimidin-4-phenyl)-2-fluoro-3-(trifluoromethyl)benzamide

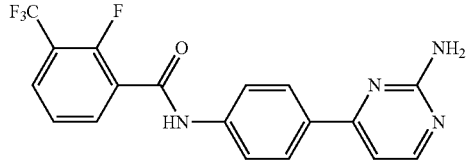 [SMILES: Nc1nccc(-c2ccc(NC(=O)c3cccc(C(F)(F)F)c3F)cc2)n1]

$^1$H NMR (600 MHz, DMSO-d$_6$) δ 11.2 (s, 1H), 8.5 (d, J=6.5 Hz, 1H), 8.3-8.3 m, 2H), 8.1-8.0 (m, 1H), 8.0 (dd, J=7.7, 5.4 Hz, 3H), 7.6 (t, J=6.9 Hz, 2H), $^{13}$C NMR (151 MHz, DMSO) δ 162.4, 157.2, 156.5, 155.5, 143.6, 135.5, 135.5, 129.9, 129.9, 126.7, 126.6, 125.7, 125.7, 123.8, 122.0, 120.2, 105.9.

Example 15

Compound 11 below was prepared by the following method.

Compound 11: N-(4-(2-(N,N-di-t-butyloxycarbonyl)aminopyrimidin-4-yl)phenyl)-2-fluorobenzamide

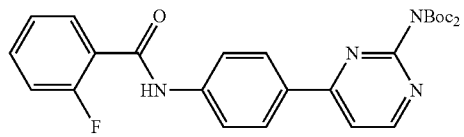

Compound E (100 mg, 0.5 mmol), 1-ethyl-3-(3-dimethylaminopropyl)carbodiimide (100 mg, 1.3 mmol), and 4-(dimethylamino)pyridine (80 mg, 2.5 mmol) were dissolved in dimethylformamide (2 mL), and then 2-fluorobenzoic acid (72 mg, 1.3 mmol) was added, and then stirred at ambient temperature for 12 hours.

The mixture was diluted with an ammonium chloride solution. The organic layer was dried over anhydrous magnesium sulfate, and the solvent was concentrated under vacuum and purified using column chromatography (hexane:ethyl acetate=1:1).

1H NMR (600 MHz, Chloroform-d) δ 8.8 (d, J=5.3 Hz, 1H), 8.7 (d, 15.7 Hz, 1H), 8.2 (td, J=7.9, 1.9 Hz, 1H), 8.1-8.1 (m, 2H), 7.8-7.8 (m, 2H), 7.6 (d, J=5.3 Hz, 1H), 7.6-7.5 (m, 1H), 7.3 (td, J=7.6, 1.1 Hz, 1H), 7.2 (ddd, J=12.3, 8.3, 1.1 Hz, 1H), 1.5 (s, 19H), $^{13}$C NMR (151 MHz, CDCl$_3$) δ 164.9, 161.5, 161.5, 161.2, 159.6, 158.9, 150.9, 140.7, 132.3, 132.3, 131.8, 128.3, 125.3, 125.2, 120.4, 116.3, 116.2, 113.8, 83.3, 27.9.

Example 16

Compound 12 below was prepared in the same manner as in Example 15 above.

Compound 12: N-(4-(2-1N,N-di-t-butyloxycarbonyl)aminopyrimidin-4-yl)phenyl)-3-fluorobenzamide

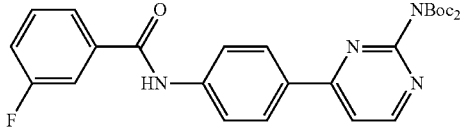

1H NMR (600 MHz, Chloroform-d) δ 8.6-8.6 (m, 2H), 8.0-7.9 (m, 2H), 7.7-7.6 (m, 4H), 7.5-7.4 (m, 2H), 7.2 (td, J=8.3, 2.6 Hz, 1H), 1.5 (s, 18H), 13C NMR (151 MHz, CDCl3) δ 165.0, 164.7, 164.7, 163.6, 161.9, 158.8, 158.6, 151.3, 141.1, 136.8, 136.8, 130.9, 127.9, 122.9, 122.9, 120.1, 119.1, 114.7, 113.9, 83.7, 27.9, Example 17

Compound 13 below was prepared in the same manner as in Example 15 above.

Compound 13: N-(4-(2-(N,N-di-t-butyloxycarbonyl)aminopyrimidin-4-yl)phenyl)-4-fluorobenzamide

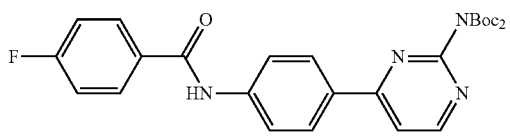

1H NMR (600 MHz, Chloroform-d) δ 8.6-8.6 (m, 1H), 8.5 (s, 1H), 8.0 (dt, J=9.1, 3.3 Hz, 4H), 7.7-7.7 (m, 2H), 7.4 (dd, J=5.3, 1.6 Hz, 1H), 7.2-7.1 (m, 2H), 1.5 (d, J=1.7 Hz, 19H), 13C NMR (151 MHz, CDCl$_3$) δ165.9, 165.1, 164.9, 158.8, 158.6, 151.3, 141.2, 130.8, 129.9, 128.0, 120.1, 115.8, 113.9, 83.7, 27.9.

Example 18

Compound 14 below was prepared in the same manner as in Example 15 above.

Compound 14: N-(4-(2-(N,N-di-t-butyloxycarbonyl)aminopyrimidin-4-yl)phenyl)-3-chlorobenzamide

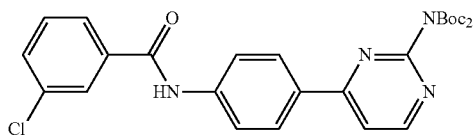

1H NMR (600 MHz, Chloroform-d) δ 8.6 (d, J=5.3 Hz, 1H), 8.5 (s, 1H), 8.0 (d, J=8.6 Hz, 2H), 7.9 (t, J=1.9 Hz, 1H), 7.8 (dt, J=7.7, 1.4 Hz, 1H), 7.7 (d, J=8.5 Hz, 2H), 7.5 (ddd, J=8.0, 2.2, 1.1 Hz, 1H), 7.5 (d, J=5.3 Hz, 1H), 7.4 (t, J=7.8 Hz, 1H), 1.5 (s, 18H), 13C NMR (151 MHz, CDCl$_3$) δ 165.0, 164.6, 158.8, 158.6, 151.2, 140.9, 136.3, 134.9, 132.0, 131.1, 130.0, 128.1, 127.7, 125.4, 120.1, 113.9, 83.7, 27.9.

Example 19

Compound 15 below was prepared in the same manner as in Example 15 above.

Compound 15: N-(4-(2-(N,N-di-t-butyloxycarbonyl)aminopyrimidin-4-yl)phenyl)-4-(trifluoromethyl)benzamide

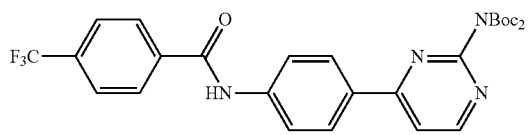

1H NMR, (600 MHz, Chloroform-d) δ 8.7 (s, 1H), 8.6 (d, J=5.3 Hz, 1H), 8.1-8.0 (m, 2H), 7.9 (d, J=8.7 Hz, 2H), 7.7 (d, J=8.1 Hz, 2H), 7.7 (d, J=8.7 Hz, 2H), 7.4 (d, J=5.3 Hz, 1H), 1.5 (s, 18H), 13C NMR (151 MHz, CDCl$_3$) δ165.1, 164.8, 158.7, 158.5, 151.4, 140.9, 137.9, 130.9, 130.5, 127.9, 125.7, 120.2, 113.9, 83.9, 27.9.

Example 20

Compound 16 below was prepared by the following method.

Compound 16: N-(4-(2-aminopyrimidin-4-yl)phenyl)-2-fluorobenzamide

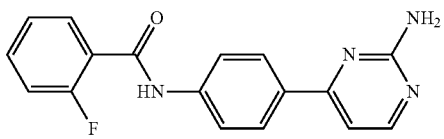 [SMILES: Nc1nccc(-c2ccc(NC(=O)c3ccccc3F)cc2)n1]

4-Normal hydrogen chloride (1.3 mL) dissolved in dioxane was added to Compound F (67 mg, 0.1 mmol) of Scheme 4 above, and the mixture was stirred at room temperature for 12 hours. The solvent was concentrated by evaporation under vacuum and then recrystallized.

1H NMR (600 MHz, DMSO-d$_6$) δ 10.9 (s, 1H), 8.5 (d, J=6.5 Hz, 1H), 8.3 (d, J=8.8 Hz, 2H), 8.0 (d, J=8.5 Hz, 2H), 7.7 (td, J=7.4, 1.8 Hz, 1H), 7.6-7.5 (m, 2H), 7.4-7.3 (m, 2H), 13C NMR (151 MHz, DMSO) δ 163.8, 160.2, 158.6, 156.5, 143.9, 133.4, 133.4, 130.5, 130.4, 129.8, 129.5, 125.1, 125.1, 120.0, 105.9, 66.8.

Example 21

Compound 17 below was prepared in the same manner as in Example 20 above.

Compound 17: N-(4-(2-aminopyrimidin-4-yl)phenyl-3-fluorobenzamide

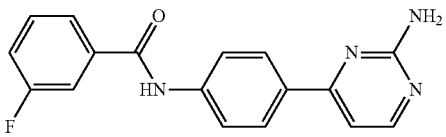

1H NMR (600 MHZ, DMSO-d6) δ 10.8 (s, 1H), 8.5 (d, J=6.6 Hz, 1H), 8.3 (d, J=8.9 Hz, 2H), 8.1 (d, J=8.9 Hz, 2H), 7.9-7.8 (m, 2H), 7.6-7.5 (m, 2H), 7.5-7.4 (m, 1H), 13C NMR (151 MHz, DMSO) δ 165.1, 163.2, 161.5, 156.4, 144.2, 137.2, 131.1, 129.7, 124.7, 120.6, 119.3, 115.3, 105.9, 66.8, 63.3.

Example 22

Compound 18 below was prepared in the same manner as in Example 20 above.

Compound 18: N-(4-(2-aminopyrimidin-4-yl)phenyl)-4-fluorobenzamide

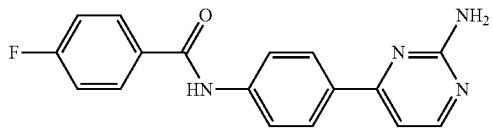

1H NMR (600 MHz, DMSO-$d_6$) δ 10.8 (s, 1H), 8.5 (d, J=6.5 Hz, 1H), 8.3-8.2 (m, 2H), 8.2-8.1 (m, 2H), 8.1-8.0 (m, J=6.6 Hz, 1H), 7.6-7.5 (d, J=6.6 Hz, 1H), 7.4-7.4 (m, 2H), 13C NMR (151 MHz, DMSO) δ 165.6, 165.4, 163.9, 156.6, 144.4, 131.3, 131.3, 131.2, 131.2, 129.6, 120.5, 115.9, 115.8, 105.9.

Example 23

Compound 19 below was prepared in the same manner as in Example 20 above.

Compound 19: N-(4-(2-aminopyrimidin-4-yl)phenyl)-3-chlorobenzamide

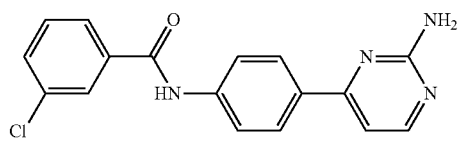

1H NMR (600 MHz, DMSO-$d_6$) δ 10.8 (s, 1H), 8.5 (d, J=6.5 Hz, 1H), 8.3-8.2 (m, 2H), 8.1-8.0 (m, 3H), 8.0 (dt, J=7.7, 1.3 Hz, 1H), 7.7 (ddd, J=8.0, 2.2, 1.0 Hz, 1H), 7.6-7.5 (m, 2H), 13C NMR (151 MHz, DMSO) δ 165.1, 156.6, 144.1, 136.9, 133.7, 132.2, 130.9, 129.6, 128.1, 127.2, 120.6, 105.9, 63.3.

Example 24

Compound 20 below was prepared in the same manner as in Example 20 above.

Compound 20: N-(4-(2-aminopyrimidin-4-yl)phenyl)-4-(trifluoromethyl)benzamide

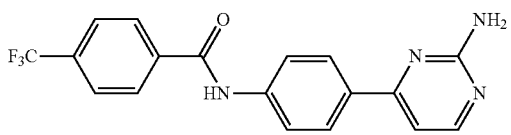

1H NMR (600 MHz, DMSO-d6) δ 11.0 (s, 1H), 8.5 (d, J=6.5 Hz, 1H), 8.3 (d, J=8.9 Hz, 2H), 8.2-8.2 (m, 2H), 8.1 (d, J=8.9 Hz, 2H), 7.9 (d, J=8.2 Hz, 2H), 7.6 (d, J=6.6 Hz, 1H), 13C NMR (151 MHz, DMSO) δ 165.4, 156.6, 144.1, 138.7, 132.2, 129.6, 129.3, 125.9, 125.9, 125.2, 123.4, 120.7, 105.9, 66.8.

Example 5

Compound 21 below was prepared in the same manner as in Example 20 above.

Compound 21: N-(4-(2-aminopyrimidin-4-yl)phenyl)-4-phenoxybenzamide

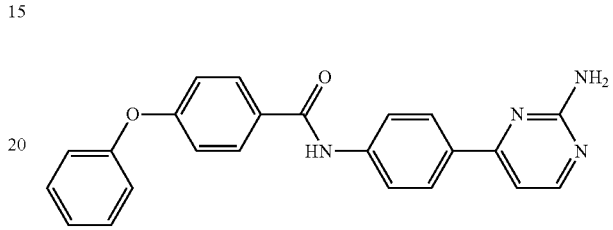

1H NMR (600 MHz, DMSO-d6) δ 10.7 (s, 1H), 8.5 (d, J=6.5 Hz, 1H), 8.3-8.2 (m, 2H), 8.1-8.0 (m, 4H), 7.5 (d, J=6.6 Hz, 1H), 7.5-7.4 (m, 2H), 7.2-7.2 (m, 1H), 7.1-7.0 (m, 4H), 13C NMR (151 MHz, DMSO) δ 165.7, 160.6, 156.5, 155.8, 144.6, 130.8, 129.6, 129.3, 129.1, 124.9, 120.5, 120.2, 117.8, 105.9.

Example 26

Compound 22 below was prepared by the following method.

Compound 22: N-(4-(2-(N,N-di-t-butyloxycarbonyl)aminopyrimidin-4-yl)phenyl)benzamide

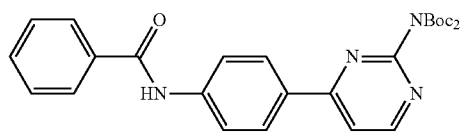

Compound E (100 mg, 0.3 mmol) and 4-(dimethylamino)pyridine (79 mg, 0.6 mmol) were dissolved in dichloromethane (1 mL), and then benzoyl chloride (0.1 mL, 0.8 mmol) was added, and then stirred at ambient temperature for 12 hours. The mixture was diluted with an ammonium chloride solution. The organic layer was dried over anhydrous magnesium sulfate, and the solvent was concentrated under vacuum and purified using column chromatography (hexane:ethyl acetate=1:1).

1H NMR (600 MHz, Chloroform-d) δ 8.6 (d, J=5.3 Hz, 1H), 8.5 (s, 1H), 8.0-8.0 (m, 2H), 7.9 (dt, J=7.0, 1.4 Hz, 2H), 7.8-7.7 (m 2H), 7.6-7.5 (m, 1H), 7.5-7.4 (m, 31-1), 1.5 (s, 18H), 13C NMR (151 MHz, CDCl$_3$) δ 165.9, 165.0, 158.8, 158.7, 151.2, 141.3, 134.6, 132.0, 130.9, 128.7, 128.0, 127.3, 120.1, 113.8, 83.5, 27.9.

Example 27

Compound 23 below was prepared in the same manner as in Example 2.6 above.

Compound 23: N-(4-(2-N,N-di-t-butyloxycarbonyl)aminopyrimidin-4-yl)phenyl)-2-methoxybenzamide

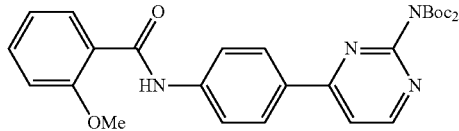

1H NMR (600 MHz, Chloroform-d) δ 10.0 (s, 1H), 8.7 (d, J=5.3 Hz, 1H), 8.3 (dd, J=7.8, 1.9 Hz, 1H), 8.1-8.1 (m, 2H), 7.9-7.8 (m, 2H), 7.6 (d, J=5.3 Hz, 1H), 7.5 (ddd, J=8.3, 7.3, 1.9 Hz, 1H), 7.2-7.1 (m, 1H), 7.0 (dd, J=8.4, 1.0 Hz, 1H), 4.1 (s, 3H), 1.4 (s, 19H), 13C NMR (151 MHz, CDCl$_3$) δ 165.1, 163.5, 158.8, 157.2, 150.8, 141.4, 133.7, 132.5, 131.1, 128.2, 121.8, 121.4, 120.3, 113.7, 111.6, 83.2, 56.3, 27.9.

Example 28

Compound 24 below was prepared in the same manner as in Example 26 above.

Compound 24: N-(4-(2-N,N-di-t-butyloxycarbonyl)aminopyrimidin-4-yl)phenyl)-4-nitrobenzamide

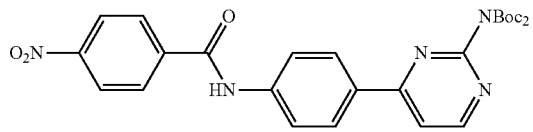

1H NMR (600 Chloroform-d) δ 9.1 (s, 1H), 8.6 (d, J=5.2 Hz, 1H), 8.3 (d, J=8.3 Hz, 2H), 8.1 (d, J=8.4 Hz, 2H), 8.0 (d, J=8.3 Hz, 2H), 7.7 (d, J=8.4 Hz, 2H), 7.5 (d, J=5.3 Hz, 1H), 1.5 (s, 19H), 13C NMR (151 CDCl$_3$) δ 165.0, 164.0, 158.9, 158.6, 151.4, 149.7, 140.9, 140.2, 131.1, 128.8, 127.9, 123.7, 120.3, 113.9, 83.9, 27.9.

Example 29

Compound 25 below was prepared in the same manner as in Example 26 above.

Compound 25: N-(4-(2-N,N-di-t-butyloxycarbonyl)aminopyrimidin-4-yl)phenyl)-4-iodobenzamide

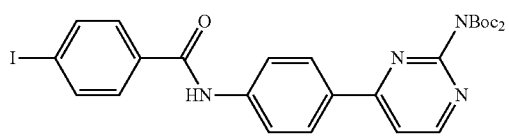

1H NMR (600 MHz, Chloroform-d) δ 8.6 (d, J=5.3 Hz, 1H), 8.0 (d, J=8.7 Hz, 2H), 7.8 (d, J=8.4 Hz, 2H), 7.7 (d, 8.7 Hz, 2H), 7.6 (d, J=8.4 Hz, 2H), 7.4 (d, J=5.3 Hz, 1H), 1.5 (s, 18H), 13C NMR (151 MHz, CDCl$_3$) δ 165.2, 165.0, 158.8, 151.3, 141.1, 137.9, 133.9, 13099, 128.9, 128.0, 120.1, 113.9, 99.2, 83.7, 27.9.

Example 30

Compound 26 below was prepared in the same manner as in Example 26 above.

Compound 26: N-(4-(2-N,N-di-t-butyloxycarbonyl)aminopyrimidin-4-yl)phenyl)-3,5-dimethylbenzamide

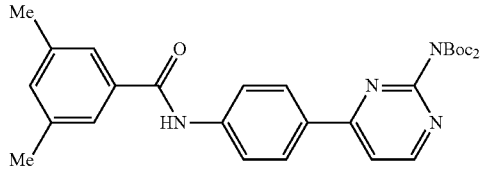

1H NMR (600 MHz, Chloroform-d) δ 8.7 (d, J=5.3 Hz, 1H), 8.2 (s, 1H), 8.1 (d, J=8.7 Hz, 2H), 7.8 (d, J=8.7 Hz, 2H), 7.5 (d, J=5.3 Hz, 1H), 7.5 (s, 2H), 7.2 (s, 1H), 2.4 (s, 6H), 1.5 (s, 19H), 13C NMR (151 MHz, CDCl$_3$) δ 166.3, 165.1, 158.9, 151.0, 141.3, 138.5, 134.6, 133.7, 131.1, 128.2, 124.9, 119.9, 113.8, 83.4, 27.9, 21.3.

Example 31

Compound 27 below was prepared in the same manner as in Example 26 above.

Compound 27: N-(4-(2-N,N-di-t-butyloxycarbonyl)aminopyrimidin-4-yl)phenyl)-4-ethylbenzamide

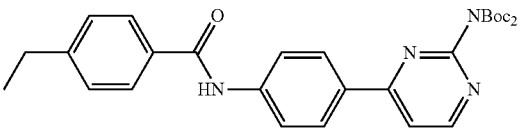

1H NMR (600 MHz, Chloroform-d) δ 8.7 (d, J=5.3 Hz, 1H), 8.3 (s, 1H), 8.0 (d, J=8.7 Hz, 2H), 7.8 (d, J=8.2 Hz, 2H), 7.8 (d, J=8.7 Hz, 2H), 7.5 (d, J=5.3 Hz, 1H), 7.3 (d, J=8.0 Hz, 2H), 2.7 (q, J=7.6 Hz, 2H), 1.5 (s, 18H), 1.3 (t, J=7.6 Hz, 4H), 13C NMR (151 MHz, CDCl3) δ 165.9, 165.1, 158.8, 158.7, 151.1, 148.9, 141.3, 131.9, 130.9, 128.3, 128.1, 127.4, 119.9, 113.8, 83.4, 28.9, 2793, 15.3.

Example 32

Compound 28 below was prepared by the following method.

Compound 28: N-(4-(2-aminopyrimidin-4-yl)phenyl)benzamide

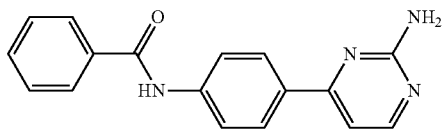 [SMILES: Nc1nccc(-c2ccc(NC(=O)c3ccccc3)cc2)n1]

4-Normal hydrogen chloride (0.6 mL) dissolved in dioxane was added to Compound F (30 mg, 0.1 mmol) of Scheme 6 above, and the mixture was stirred at room temperature for 12 hours. The solvent was concentrated by evaporation under vacuum and then recrystallized.

1H NMR (600 MHz, DMSO-d6) δ 10.7 (s, 1H), 8.4 (d, J=6.5 Hz, 1H), 8.3-8.2 (m, 2H) 8.1-8.0 (m, 2H) 8.0-8.0 (m, 2H), 7.6-7.6 (m, 1H), 7.5 (td, J=7.1, 1.5 Hz, 3H), 13C NMR (151 MHz, DMSO) δ 166.5, 156.7, 144.4, 134.9, 132.4, 129.6, 128.9, 128.3, 120.5, 105.9, 66.8.

Example 33

Compound 29 below was prepared in the same manner as in Example 32 above.

Compound 29: N-(4(2-aminopyrimidin-4-yl)phenyl)-2-methoxybenzamide

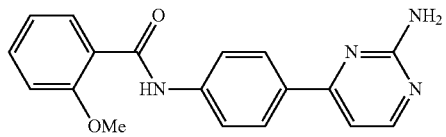 [SMILES: COc1ccccc1C(=O)Nc1ccc(-c2ccnc(N)n2)cc1]

1H NMR (600 MHz, DMSO-d6) δ10.5 (s, 1H), 8.5 (d, J=6.6 Hz, 1H), 8.3-8.2 (m, 2H), 8.0 (d, J=8.5 Hz, 2H), 7.6 (dd, J=7.6, 1.8 Hz, 1H), 7.6 (d, J=6.6 Hz, 1H), 7.5 (ddd, J=8.8, 7.3, 1.8 Hz, 1H), 7.2 (d, J=8.4 Hz 1H), 7.1-7.0 (m, 1H), 3.9 (s, 3H), 13C NMR (151 MHz, DMSO) δ 165.7, 156.9, 156.5, 144.2, 132.8, 130.1, 129.8, 129.1, 125.2, 120.9, 119.9, 112.5, 105.9, 56.4, 34.5.

Example 34

Compound 30 below was prepared in the same manner as in Example 32 above.

Compound 30: N-(4(2-aminopyrimidin-4-yl)phenyl)-4-nitrobenzamide

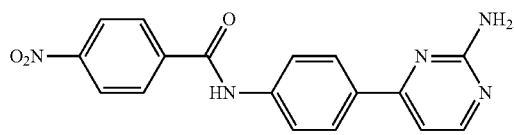 [SMILES: Nc1nccc(-c2ccc(NC(=O)c3ccc([N+](=O)[O-])cc3)cc2)n1]

1H NMR (600 MHz, DMSO-d6) δ 11.0 (s, 1H), 8.4 (d, J=6.4 Hz, 1H), 8.4-8.3 (m, 2H), 8.3-8.2 (m, 4H), 8.0 (d, J=8.8 HZ, 2H), 7.5 (d, J=6.4 Hz, 1H), 13C NMR (151 MHz, DMSO) δ 164.9, 157.8, 149.8, 143.6, 140.6, 130.2, 129.9, 129.4, 124.0, 120.7, 105.9.

Example 35

Compound 31 below was prepared in the same manner as in Example 32 above.

Compound 31:
N-(4(2-aminopyrimidin-4-yl)phenyl)-4-iodobenzamide

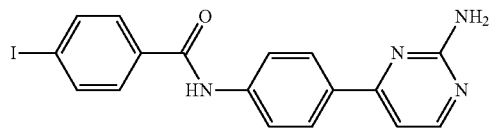 [SMILES: Nc1nccc(-c2ccc(NC(=O)c3ccc(I)cc3)cc2)n1]

1H NMR (600 MHz, DMSO-d6) δ 10.8 (s, 1H), 8.5 (d, J=6.6 Hz, 1H), 8.2 (d, J=8.9 Hz, 2H), 8.0 (d, J=8.9 Hz, 2H), 7.9 (d, J=8.5 Hz, 2H), 7.8 (d, J=8.5 Hz, 2H), 7.6 (d, J==6.6 Hz, 1H), 13C NMR (151 MHz, DMSO) δ 165.8, 156.3, 144.4, 137.8, 134.2, 131.3, 130.3, 129.7, 129.3, 120.6, 114.3, 1059, 100.4.

Example 36

Compound 32 below was prepared in the same manner as in Example 32 above.

Compound 32:
N-(4-(2-aminopyrimidin-4-yl)-3,5-dimethylbenzamide

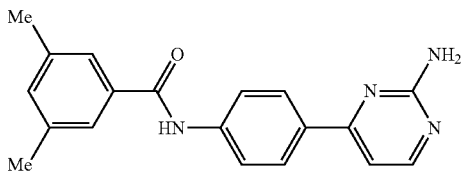 [SMILES: Cc1cc(C)cc(C(=O)Nc2ccc(-c3ccnc(N)n3)cc2)c1]

1H NMR (600 MHz, DMSO-d6) δ 10.6 (s, 1H), 8.5 (d, J=6.6 Hz, 1H), 8.3-8.2 (m, 2H), 8.1-8.0 (m, 2H), 7.6 (d, J=1.6 Hz, 2H), 7.6 (d, J=6.6 Hz, 1H), 7.2 (s, 1H), 2.3 (s, 6H), 13C NMR (151 MHz, DMSO) δ 166.7, 156.4, 144.6, 138.1, 134.9, 133.7, 129.7, 129.1, 126.0, 120.4, 105.9, 21.3.

Example 37

Compound 33 below was prepared in the same manner as in Example 32 above.

Compound 33: N-(4-(2-aminopyrimidin-4-yl)phenyl)-4-ethylbenzamide

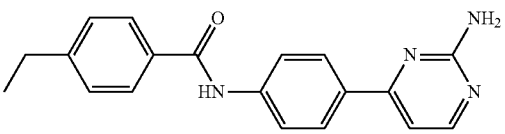

1H NMR (600 MHz, DMSO-d6) δ 10.7 (s, 1H), 8.5 (d, J=6.6 Hz, 1H), 8.3-8.2 (m, 2H), 8.1-8.0 (m, 2H), 8.0-7.9 (m, 2H), 7.6 (d, J=6.6 Hz, 1H), 7.4 (d, J=8.2 Hz, 2H), 2.7 (q, J=7.6 Hz, 2H), 1.2 (t, J=7.6 Hz, 3H), 13C NMR (151 MHz, DMSO) δ 167.7, 166.4, 156.2, 148.7, 144.7, 132.3, 129.9, 129.7, 128.5, 128.4, 128.3, 120.5, 105.9, 28.6, 15.8.

Test Example

Enzyme Activation Experiment

A sufficient amount of cells was obtained by culturing the INS-1 cell line under general cell culture condition (37° C. 5% $CO_2$). Immediately before use in the experiment, a culture dish of the INS-1 cells was placed on ice, the culture medium was removed, and then washed with cold phosphate-buffered saline (PBS) (WELGEME, LB 001-02) to obtain a cell pellet.

To the harvested cell pellet, an appropriate amount of ice-cold Assay Buffer contained in the Glutamate Dehydrogenase (GDH) Activity Colorimetric Assay Kit (BioVision, K729-100) was added and then homogenized in the tube.

The tube was subjected to centrifuge in a condition of 13,000 g, 4° C. for 10 minutes, and then the pellet was discarded, and only the supernatant was collected and transferred to a new tube to obtain a cell lysate. Then, the protein concentration of the cell lysate was measured using Pierce™ BCA Protein Assay kit (Thermo, 23225).

By referring to the measured protein concentration, the cell lysate was prepared by diluting its concentration to 30 μg/50 μL or 100 μg/50 μL using the Assay Buffer.

The prepared cell lysate+vehicle or compound+Reaction mix was added according to the volume determined in the protocol of the Glutamate Dehydrogenase (GDH) Activity Colorimetric Assay Kit and reacted at 37° C., and the absorbance at 450 nm was measured using a kinetic method.

The GDH activity was calculated according to the calculation formula shown in the Assay Kit, and then the activity of the group treated with the vehicle was set to 1, and the folds of the remaining groups were calculated, and the results are shown in Table 2 below and FIG. 1.

TABLE 2

|  | Concentration (μM) | Enzyme activity (fold) |
|---|---|---|
| DMSO | — | 1 |
| Compound 6 | 0.2 | 2.14 |
|  | 2 | 6.93 |
| Compound 7 | 0.2 | 1.94 |
|  | 2 | 3.23 |
| Compound 8 | 0.2 | 1.34 |
|  | 2 | 11.05 |
| Compound 9 | 0.2 | 1.13 |
|  | 2 | 6.43 |
| Compound 10 | 0.2 | 2.08 |
|  | 2 | 10.83 |

That is, it was found that the compounds of the present invention exhibit excellent GDH activity.

The invention claimed is:

1. A compound or pharmaceutically acceptable salt thereof, wherein the compound is selected from the group consisting of the following compounds:

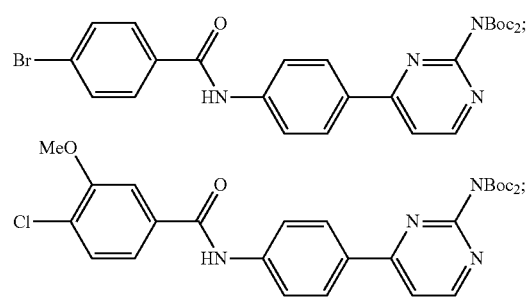

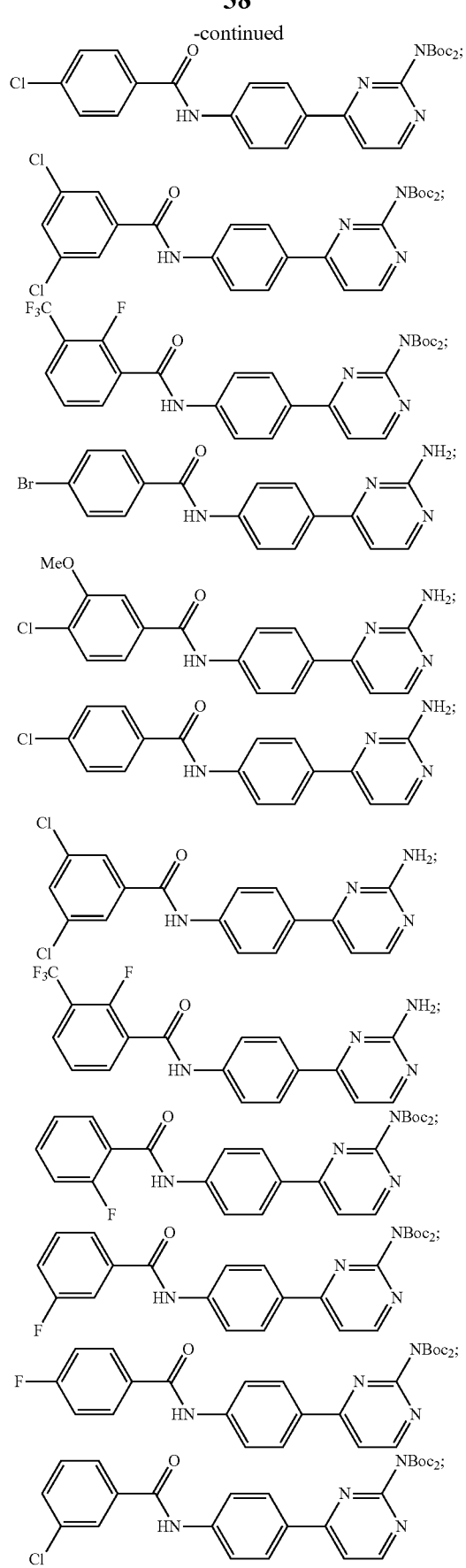

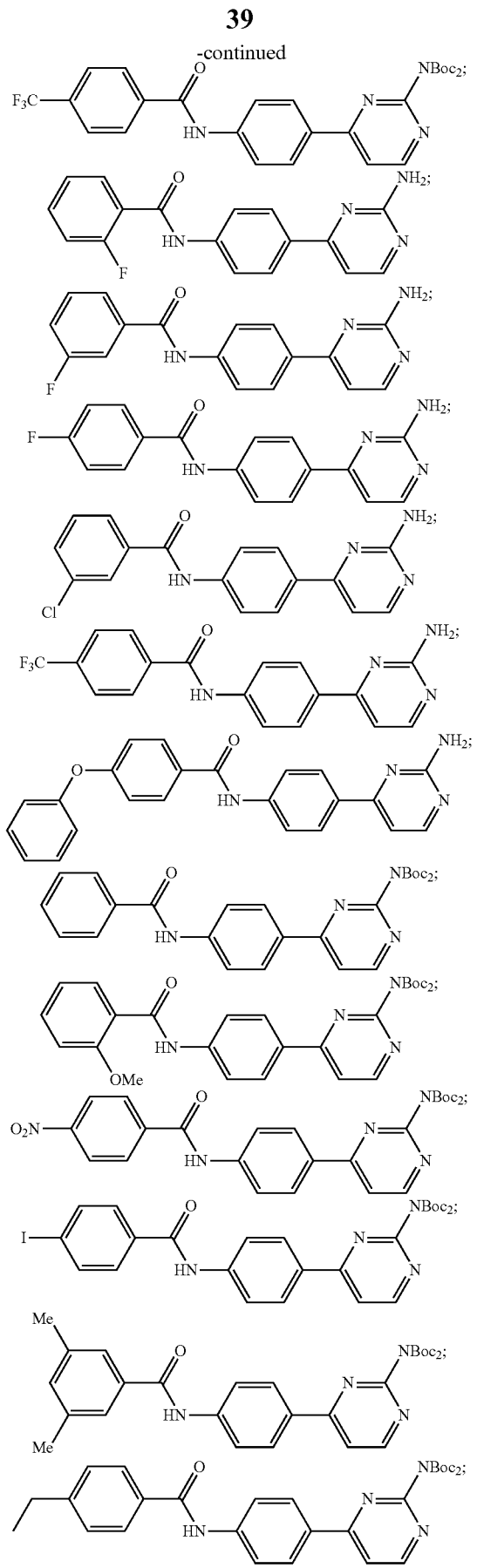
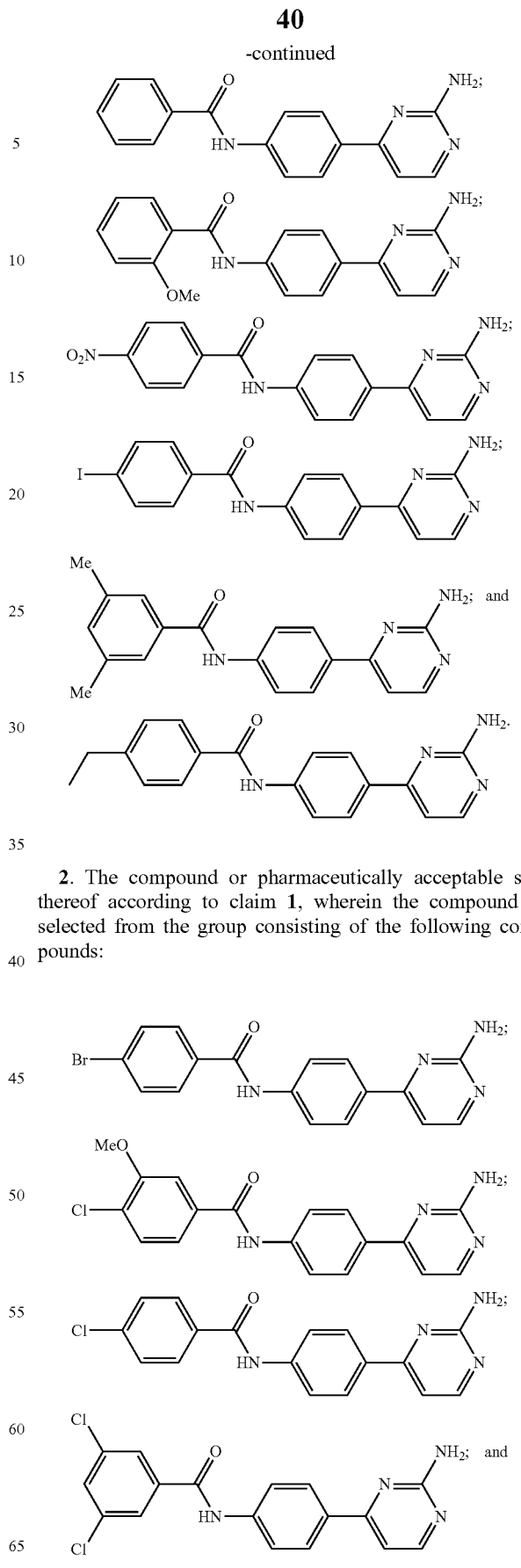
2. The compound or pharmaceutically acceptable salt thereof according to claim 1, wherein the compound is selected from the group consisting of the following compounds:

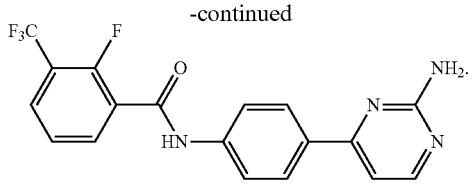

3. A pharmaceutical composition for treating obesity, diabetes, or fatty liver, comprising the compound of claim 1 or pharmaceutically acceptable salt thereof.

4. A method for treating obesity, diabetes, or fatty liver, comprising administering an effective amount of the compound of claim 1 or pharmaceutically acceptable salt thereof to a patient with obesity, diabetes, or fatty liver.

5. The compound or pharmaceutically acceptable salt thereof according to claim 1, wherein the compound is selected from the group consisting of the following compounds:

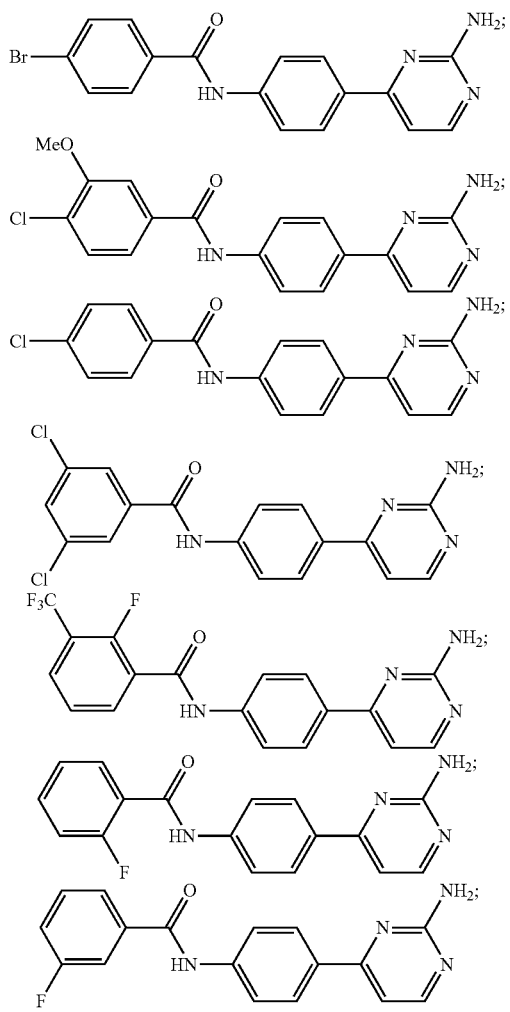

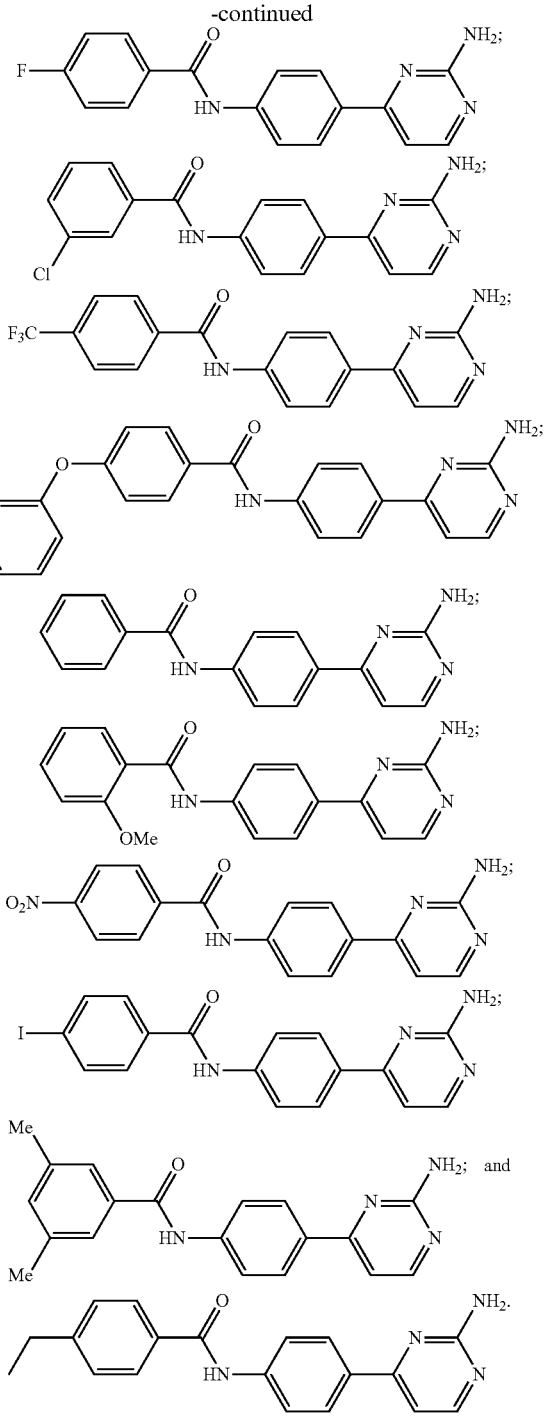

6. A pharmaceutical composition for treating obesity, diabetes, or fatty liver, comprising the compound of claim 5 or pharmaceutically acceptable salt thereof.

* * * * *